(12) United States Patent
Ogilvie et al.

(10) Patent No.: US 6,673,791 B2
(45) Date of Patent: Jan. 6, 2004

(54) NON-NUCLEOSIDE REVERSE TRANSCRIPTASE INHIBITORS

(75) Inventors: William W. Ogilvie, Ottawa (CA); Robert Déziel, Mont-Royal (CA); Jeffrey O'Meara, Laval (CA); Bruno Simoneau, Laval (CA)

(73) Assignee: Boehringer Ingelheim (Canada) Ltd., Laval (CA)

( * ) Notice: Subject to any disclaimer, the term of this patent is extended or adjusted under 35 U.S.C. 154(b) by 0 days.

(21) Appl. No.: 10/205,094

(22) Filed: Jul. 25, 2002

(65) Prior Publication Data

US 2003/0171363 A1 Sep. 11, 2003

Related U.S. Application Data

(60) Provisional application No. 60/308,710, filed on Jul. 30, 2001.

(51) Int. Cl.$^7$ .................. C07D 471/14; A61K 31/55
(52) U.S. Cl. ........................ 514/220; 540/495
(58) Field of Search ................ 540/495; 514/220

(56) References Cited

U.S. PATENT DOCUMENTS

| 5,366,972 A | 11/1994 | Hargrave et al. ............ 514/220 |
| 5,705,499 A | 1/1998 | Cywin et al. ................ 514/220 |

FOREIGN PATENT DOCUMENTS

| WO | WO 01/96338 A1 | 12/2001 |

OTHER PUBLICATIONS

Hargrave, et al; "Novel, Non–Nucleoside Inhibitors of HIV–1 Reverse Transcriptase. 1. Tricyclic Pyridobenzo– and Dipyridodiazepinones"; J. Med. Chem., 1991, 34, 2231–2241.

Cywin, et al; "Novel Nonnucleoside Inhibitors of HIV–1 Reverse Transcriptase. 8. 8–Aryloxymethyl– and 8–Arylthiomethyldipyridodiazepinones1"; J. Med. Chem., 1998, 41. 2972–2984.

Klunder, et al; "Novel Nonnucleoside Inhibitors of HIV–1 Reverse Transcriptase. 7. 8–Arylethyldipyridodiazepinones As Potent Broad–Spectrum Inhibitors Of Wild–Type And Mutant Enzymes"; J. Med. Chem. 1998, 41, 2960–2971.

Primary Examiner—Bruck Kifle
(74) Attorney, Agent, or Firm—Robert P. Raymond; Alan R. Stempel; Mary-Ellen M. Devlin

(57) ABSTRACT

Compounds represented by formula I:

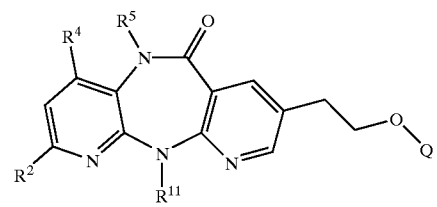

wherein $R^2$ is H, halogen, $NHNH_2$, $(C_{1-4})$alkyl, $O(C_{1-6})$alkyl, and haloalkyl; $R^4$ is H or Me; $R^5$ is H or $(C_{1-4})$alkyl; $R^{11}$ is $(C_{1-4})$alkyl, $(C_{1-4})$alkyl$(C_{3-7})$cycloalkyl, or $(C_{3-7})$cycloalkyl; and Q is naphthyl, fused phenyl$(C_{4-7})$cycloalkyl and fused phenyl-5, 6, or 7-membered saturated heterocycle having one to two heteroatom selected from O, N, or S, said Q being substituted with from 1 to 4 $R^{12}$ substituents selected from: $R^{13}$, $(C_{1-6})$alkyl, $(C_{3-7})$cycloalkyl, or $(C_{2-6})$alkenyl, said alkyl, cycloalkyl, or alkenyl being optionally substituted with $R^{13}$; or a salt thereof. Compounds represented by formula I have inhibitory activity against Wild Type, single and double mutant strains of HIV.

40 Claims, No Drawings

NON-NUCLEOSIDE REVERSE TRANSCRIPTASE INHIBITORS

RELATED APPLICATIONS

Benefit of U.S. Provisional Application Serial No. 60/308,710, filed on Jul. 30, 2001 is hereby claimed.

TECHNICAL FIELD OF THE INVENTION

The invention relates to novel compounds and pharmaceutically acceptable salts thereof, their use, either alone or in combination with other therapeutic agents, in the treatment or prophylaxis of HIV infection, and to pharmaceutical compositions comprising the compounds that are active against NNRTI resistant mutants.

BACKGROUND OF THE INVENTION

The disease known as acquired immune deficiency syndrome (AIDS) is caused by the human immunodeficiency virus (HIV), particularly the strain known as HIV-1. In order for HIV to be replicated by a host cell, the information of the viral genome must be integrated into the host cell's DNA. However, HIV is a retrovirus, meaning that its genetic information is in the form of RNA. The HIV replication cycle therefore requires a step of transcription of the viral genome (RNA) into DNA, which is the reverse of the normal chain of events. An enzyme that has been aptly dubbed reverse transcriptase (RT) accomplishes the transcription of the viral RNA into DNA. The HIV virion includes a copy of RT along with the viral RNA.

Reverse transcriptase has three known enzymatic functions; it acts as an RNA-dependent DNA polymerase, as a ribonuclease, and as a DNA-dependent DNA polymerase. Acting as an RNA-dependent DNA polymerase, RT transcribes a single-stranded DNA copy of the viral RNA. Acting as a ribonuclease, RT destroys the original viral RNA, and frees the DNA just produced from the original RNA. Finally, acting as a DNA-dependent DNA polymerase, RT makes a second, complementary DNA strand, using the first DNA strand as a template. The two strands form double-stranded DNA, which is integrated into the host cell's genome by another enzyme called integrase.

Compounds that inhibit the enzymatic functions of HIV-1 reverse transcriptase will inhibit replication of HIV-1 in infected cells. Such compounds are useful in the prevention or treatment of HIV-1 infection in human subjects, as demonstrated by known RT inhibitors such as 3'-azido-3'-deoxythymidine (AZT), 2',3'-dideoxyinosine (ddI), 2',3'-dideoxycytidine (ddC), d4T, 3TC, Nevirapine, Delavirdine, Efavirenz, Abacavir, and Tenofovir, the main drugs thus far approved for use in the treatment of AIDS.

As with any antiviral therapy, use of RT inhibitors in the treatment of AIDS eventually leads to a virus that is less sensitive to the given drug. Resistance (reduced sensitivity) to these drugs is the result of mutations that occur in the reverse transcriptase segment of the pol gene. Several mutant strains of HIV have been characterised, and resistance to known therapeutic agents is believed to be due to mutations in the RT gene. One of the more commonly observed mutants clinically for the non-nucleoside reverse transcriptase inhibitors, is the Y181C mutant, in which a tyrosine (Y), at codon 181, has been mutated to a cysteine (C) residue. Other mutants, which emerge with increasing frequency during treatment using known antivirals, include single mutants K103N, V106A, G190A, Y188C, and P236L, and double mutants K103N/Y181C, K103N/P225H, K103N/V108I and K103N/L100I.

As antiviral use in therapy and prevention of HIV infection continues, the emergence of new resistant strains is expected to increase. There is therefore an ongoing need for new inhibitors of RT, which have different patterns of effectiveness against the various resistant mutants.

Compounds having tricyclic structures, which are inhibitors of HIV-1, are described in U.S. Pat. No. 5,366,972. Other inhibitors of HIV-1 reverse transcriptase are described in Hargrave et al., J. Med Chem., 34, 2231 (1991), Cywin et al., J. Med. Chem., 41, 2972 (1998) and Klunder et al., J. Med. Chem., 41, 2960 (1998).

U.S. Pat. No. 5,705,499 proposes 8-arylalkyl- and 8-arylheteroalkyl-5,11-dihydro-6H-dipyrido[3,2-B:2',3'-E][1,4]diazepines as inhibitors of RT. The exemplified compounds are shown to have some activity against HIV WT reverse transcriptase.

WO 01/96338A1 discloses diazepine structures having quinoline and quinoline-N-oxide substituents as inhibitors of RT. The exemplified compounds have activity against HIV WT, single and double mutant strains.

SUMMARY OF THE INVENTION

The invention provides novel fused ring-containing compounds that are potent inhibitors of wild-type (WT) and double mutant strains of HIV-1 RT, particularly the double mutation K103N/Y181C.

In a first aspect the invention provides compounds represented by formula I:

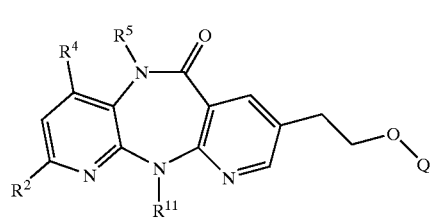

wherein $R^2$ is selected from the group consisting of H, halogen, $NHNH_2$, $(C_{1-4})$alkyl, $O(C_{1-6})$alkyl, and haloalkyl;

$R^4$ is H or Me;

$R^5$ is H or $(C_{1-4})$alkyl;

$R^{11}$ is $(C_{1-4})$alkyl, $(C_{1-4})$alkyl$(C_{3-7})$cycloalkyl, or $(C_{3-7})$cycloalkyl; and Q is naphthyl, fused phenyl$(C_{4-7})$cycloalkyl and fused phenyl-5, 6, or 7-membered saturated heterocycle having one to two heteroatom selected from O, N, or S, said Q being substituted with from 1 to 4 $R^{12}$ substituents selected from: $R^{13}$, $(C_{1-6})$alkyl, $(C_{3-7})$cycloalkyl, or $(C_{2-6})$alkenyl, said alkyl, cycloalkyl, or alkenyl being optionally substituted with $R^{13}$, wherein $R^{13}$ is defined as:

a) $NR^{13a}COR^{13b}$ wherein $R^{13a}$ and $R^{13b}$ are each independently H, $(C_{1-6})$alkyl, $(C_{3-7})$cycloalkyl or $(C_{1-6})$alkyl-$(C_{3-7})$cycloalkyl, said alkyl, cycloalkyl or alkyl-cycloalkyl being optionally substituted with $R^{14}$;

b) $NR^{13c}SO_2R^{13d}$ wherein $R^{13c}$ is H, $(C_{1-6})$alkyl, $(C_{3-7})$cycloalkyl or $(C_{1-6})$alkyl-$(C_{3-7})$cycloalkyl and $R^{13d}$ is $(C_{1-6})$alkyl, haloalkyl, $(C_{3-7})$cycloalkyl or $(C_{1-6})$alkyl-$(C_{3-7})$cycloalkyl, said alkyl, cycloalkyl or alkyl-cycloalkyl being optionally substituted with $R^{14}$;

c) COR$^{13e}$ wherein R$^{13e}$ has the same definition as R$^{13d}$;
d) COOR$^{13f}$ wherein R$^{13f}$ has the same definition as R$^{13c}$;
e) CONR$^{13g}$R$^{13h}$ wherein R$^{13g}$ and R$^{13h}$ are both independently H, (C$_{1-6}$)alkyl, (C$_{3-7}$)cycloalkyl, or (C$_{1-6}$)alkyl-(C$_{3-7}$)cycloalkyl; or both R$^{13g}$ and R$^{13h}$ are covalently bonded together and to the nitrogen to which they are both bonded to form a 5, 6, or 7-membered saturated heterocycle; or R$^{13h}$ is N(R$^{13i}$)$_2$ wherein each R$^{13i}$ is independently H, (C$_{1-6}$)alkyl, (C$_{3-7}$)cycloalkyl, or (C$_{1-6}$)alkyl-(C$_{3-7}$) cycloalkyl or both R$^{13i}$ are covalently bonded together and to the nitrogen to which they are both bonded to form a 5, 6, or 7-membered saturated heterocycle, said alkyl, cycloalkyl, alkyl-cycloalkyl or heterocycle being optionally substituted with R$^{14}$;
f) CONR$^{13j}$SO$_2$R$^{13k}$ wherein R$^{13j}$ has the same definition as R$^{13c}$ and R$^{13k}$ has the same definition as R$^{13d}$; or
g) SO$_2$R$^{13l}$ wherein R$^{13l}$ is (C$_{1-6}$)alkyl, (C$_{3-7}$)cycloalkyl, or (C$_{1-6}$)alkyl-(C$_{3-7}$)cycloalkyl; or R$^{13l}$ is NR$^{13m}$R$^{13n}$ wherein R$^{13m}$ and R$^{13n}$ are both independently H, (C$_{1-6}$)alkyl, (C$_{3-7}$)cycloalkyl, or (C$_{1-6}$) alkyl-(C$_{3-7}$)cycloalkyl; or both R$^{13m}$ and R$^{13n}$ are covalently bonded together and to the nitrogen to which they are both bonded to form a 5, 6, or 7-membered saturated heterocycle, said alkyl, cycloalkyl, alkyl-cycloalkyl or heterocycle being optionally substituted with R$^{14}$;

wherein R$^{14}$ is defined as:
COOR$^{14a}$, or CON(R$^{14b}$)$_2$ wherein R$^{14a}$ and R$^{14b}$ are both independently H, (C$_{1-6}$)alkyl, (C$_{3-7}$)cycloalkyl, or (C$_{1-6}$)alkyl-(C$_{3-7}$)cycloalkyl; or both R$^{14b}$ are covalently bonded together and to the nitrogen to which they are both bonded to form a 5, 6, or 7-membered saturated heterocycle;

as well as pharmaceutically acceptable salts, esters and prodrugs thereof.

In a first subgeneric aspect the invention provides compounds represented by formula I, wherein:
R$^2$ is selected from the group consisting of H, F, Cl, NHNH$_2$, (C$_{1-4}$ alkyl), and CF$_3$;
R$^4$ is H or Me;
R$^5$ is H or Me;
R$^{11}$ is (C$_{1-4}$ alkyl), or (C$_{3-7}$cycloalkyl); and
Q is selected from the group consisting of:

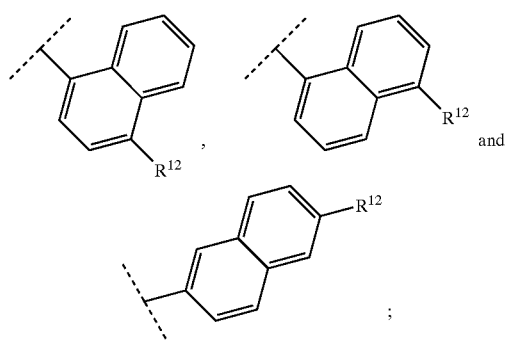

wherein
R$^{12}$ is selected from the group consisting of: COOH, (C$_{1-6}$ alkyl)COOH, (C$_{2-6}$alkenyl)COOH, (C$_{1-6}$ alkyl)COO(C$_{1-6}$ alkyl), (C$_{1-6}$ alkyl)CONH$_2$, (C$_{3-7}$ cycloalkyl)COOH, (C$_{1-6}$ alkyl)CONHNH$_2$, CH$_2$CONHSO$_2$CH$_3$, NHSO$_2$CH$_3$, NHSO$_2$CF$_3$, SO$_2$NHCOCH$_3$, SO$_2$NH$_2$, NHCO(C$_{1-4}$alkyl)COOH, NHCOCH$_2$C(CH$_3$)$_2$COOH, and SO$_2$NHCH$_2$COOH;

as well as pharmaceutically acceptable salts, esters and prodrugs thereof.

According to a second aspect of the invention, there is provided a pharmaceutical composition for the treatment or prevention of HIV infection, comprising a compound of formula I, as described herein, or a pharmaceutically acceptable salt, ester or prodrug thereof, and a pharmaceutically acceptable carrier.

According to a third aspect of the invention, there is provided a method for the treatment or prevention of HIV infection, comprising administering to a patient an HIV inhibiting amount of a compound of formula I as described herein, or a pharmaceutically acceptable salt, ester or prodrug thereof.

According to a fourth aspect of the invention, there is provided a method for the treatment or prevention of HIV infection, comprising administering to a patient an HIV inhibiting amount of a pharmaceutical composition, as described herein.

According to a fifth aspect of the invention, there is provided a method for treating or preventing HIV infection comprising administering a compound of formula I, as described herein, in combination with an antiretroviral drug.

According to a sixth aspect of the invention, there is provided a method for preventing perinatal transmission of HIV-1 from mother to baby, comprising administering a compound of formula I, as described herein, to the mother before giving birth.

DETAILED DESCRIPTION OF THE INVENTION

Definitions

The following definitions apply unless otherwise noted:
As used herein, the terms "(C$_{1-6}$)alkyl", or "(C$_{1-4}$)alkyl" either alone or in combination with another radical, are intended to mean acyclic straight or branched chain alkyl radicals containing from one to six or from one to four carbon atoms respectively. Examples of such radicals include methyl, ethyl, propyl, isopropyl, butyl, sec-butyl, tert-butyl, hexyl, 1-methylethyl, 1-methylpropyl, 2-methylpropyl, 1,1-dimethylethyl.

As used herein, the terms "(C$_{3-7}$)cycloalkyl" or "(C$_{4-7}$) cycloalkyl" are intended to mean saturated cyclic hydrocarbon radicals containing from three to seven carbon atoms or from four to seven carbon atoms respectively, and includes cyclopropyl, cyclobutyl, cyclopentyl, cyclohexyl, and cycloheptyl.

As used herein, the term "(C$_{2-6}$)alkenyl", either alone or in combination with another radical, is intended to mean an unsaturated, acyclic straight or branched chain radical containing from two to six carbon atoms.

As used herein, the term "fused phenyl(C$_{4-7}$)cycloalkyl", either alone or in combination with another radical, is intended to mean a phenyl that is fused with a (C$_{4-7}$) cycloalkyl, as defined herein.

As used herein, the term "fused phenyl-5, 6, or 7-membered saturated heterocycle", either alone or in combination with another radical is intended to mean a phenyl that is fused with a 5, 6, or 7-membered non-aromatic heterocycle having from 1 to 2 heteroatoms selected from O, N, or S. Examples include tetrahydroquinoline and tetrahydroisoquinoline.

As used herein, the term "halo" or "halogen" is intended to mean a halogen atom, and includes fluorine, chlorine, or bromine.

As used herein, the term "haloalkyl" is intended to mean an alkyl that is described above in which each hydrogen atom may be successively replaced by a halogen atom, for example $CH_2Br$ or $CH_2F$.

As used herein, the term "single or double mutant strains" means that either one or two amino acid residues that are present in WT HIV-1 strain have been replaced by residues not found in the WT strain. For example, the single mutant Y181C is prepared by site-directed mutagenesis in which the tyrosine at residue 181 has been replaced by a cysteine residue. Similarly, for the double mutant K103N/Y181C, an asparagine residue has replaced the lysine at residue 103 and a cysteine residue has replaced the tyrosine at residue 181.

As used herein, the term "pharmaceutically acceptable salt" includes those derived from pharmaceutically acceptable bases and is non-toxic. Examples of suitable bases include choline, ethanolamine and ethylenediamine. $Na^+$, $K^+$, and $Ca^{++}$ salts are also contemplated to be within the scope of the invention (also see Pharmaceutical salts, Birge, S. M. et al., J. Pharm. Sci., (1977), 66, 1–19, incorporated herein by reference).

DETAILED DESCRIPTION OF PREFERRED EMBODIMENTS

Preferably, compounds are of formula I as defined above, wherein preferably $R^2$ is selected from the group consisting of H, Cl, F, $NHNH_2$, $CH_3$, and OMe. More preferably, $R^2$ is H, Cl, F, or $CH_3$. Most preferably, $R^2$ is H, Cl, or F.

Preferably, $R^4$ is H.

Preferably, $R^5$ is Me.

Preferably, $R^{11}$ is Et.

Preferably Q is naphthyl, fused phenyl($C_{4-7}$)cycloalkyl and fused phenyl-5, 6, or 7-membered saturated heterocycle having one N atom, said Q being substituted with from 1 to 4 $R^{12}$ substituents.

More preferably, Q is selected from the group consisting of: naphthyl, tetrahydronaphthyl, indanyl, tetrahydroquinolinyl, and tetrahydroisoquinolinyl, said Q being mono- or disubstituted with $R^{12}$.

Preferably, $R^{12}$ is ($C_{1-6}$)alkyl, ($C_{2-4}$)alkenyl or ($C_{3-7}$)cycloalkyl, said alkyl, cycloalkyl or alkenyl being optionally substituted with $R^{13}$ wherein $R^{13}$ is selected from the group consisting of:

a) COOH;
b) $CONR^{13g}R^{13h}$ wherein $R^{13g}$ and $R^{13h}$ are both independently H, or ($C_{1-6}$)alkyl optionally substituted with COOH; or $R^{13h}$ is $NH_2$; and
c) $CONHSO_2CH_3$;

or $R^{12}$ is:

a) $NHCO(C_{1-6})$alkyl-COOH;
b) $NHSO_2CH_3$ or $NHSO_2CF_3$;
c) $COCH_3$ or $COCH_2COOH$;
d) $COOR^{13f}$ wherein $R^{13f}$ is H or ($C_{1-6}$)alkyl;
e) $CONR^{13g}R^{13h}$ wherein $R^{13g}$ and $R^{13h}$ are both independently H, or ($C_{1-6}$)alkyl optionally substituted with COOH; or $R^{13h}$ is $NH_2$;
f) $CONHSO_2CH_3$; or
g) $SO_2Me$, $SO_2NH_2$, $SO_2NHCOCH_3$, $SO_2NHCH_2COOH$, or $SO_2N(CH_3)_2$.

More preferably $R^{12}$ is $CH_3$, $CH_2COOH$, $(CH_2)_2COOH$, $CH(Me)COOH$, $CH(Me)CH_2COOH$, $CH_2CH(Me)COOH$, $CH_2CONH_2$, $CH_2CONHNH_2$, $CH_2CH_2CONHNH_2$, $CH_2CONHSO_2Me$,

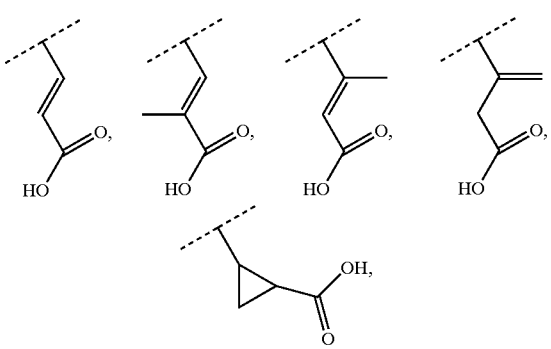

COOH, COOMe, COO-t-Bu, COMe, $COCH_2COOH$, $CONHC(Me)_2COOH$, $CONHNH_2$, CONHEt, $CONMe_2$, $NHCO(CH_2)_2COOH$, $NHCOCH_2C(Me)_2COOH$, $NHSO_2CF_3$, $NHSO_2Me$, $SO_2Me$, $SO_2NMe_2$, $SO_2NH_2$, $SO_2NHAc$, or $SO_2NHCH_2COOH$.

Even more preferably $R^{12}$ is $CH_3$, $CH_2COOH$, $(CH_2)_2COOH$, $CH_2CONH_2$, $CH_2CONHNH_2$,

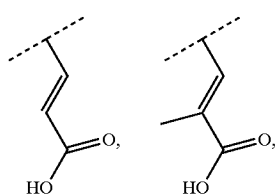

COOH, COOMe, COO-t-Bu, COMe, $CONMe_2$, $NHSO_2Me$, $SO_2Me$, $SO_2NMe_2$, $SO_2NH_2$, or $SO_2NHCH_2COOH$.

Most preferably, $R^{12}$ is $CH_2CONH_2$, $CH_2CONHNH_2$, COOH, $CONMe_2$, $NHSO_2Me$, $SO_2Me$, $SO_2NMe_2$, $SO_2NH_2$, or $SO_2NHCH_2COOH$.

Preferably, Q is

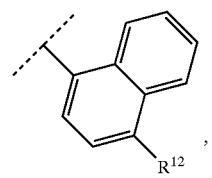

wherein, preferably $R^{12}$ is ($C_{1-6}$)alkyl, ($C_{2-4}$)alkenyl or ($C_{3-7}$)cycloalkyl, said alkyl, cycloalkyl or alkenyl being optionally substituted with $R^{13}$ wherein $R^{13}$ is selected from the group consisting of:

a) COOH;
b) $CONH_2$:
c) $CONHNH_2$; and
d) $CONHSO_2CH_3$;

or $R^{12}$ is COOH.

More preferably, $R^{12}$ is $CH_2COOH$, $(CH_2)_2COOH$, $CH(Me)COOH$, $CH(Me)CH_2COOH$, $CH_2CH(Me)COOH$, $CH_2CONH_2$, $CH_2CONHNH_2$, $CH_2CONHSO_2Me$,

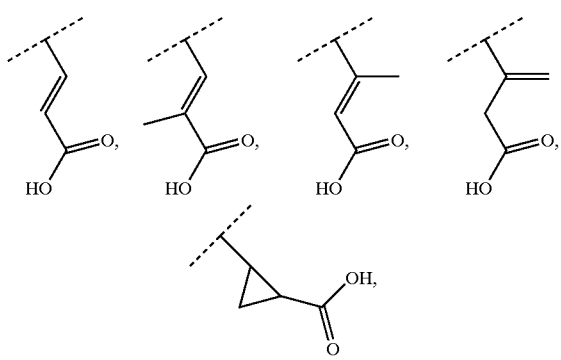

or COOH.

Even more preferably, $R^{12}$ is $CH_2COOH$, $(CH_2)_2COOH$, $CH_2CH(Me)COOH$, $CH_2CONH_2$, $CH_2CONHNH_2$,

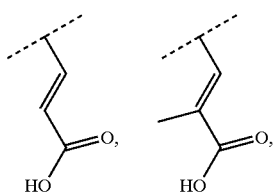

or COOH.

Most preferably, $R^{12}$ is $CH_2COOH$, $(CH_2)_2COOH$, $CH_2CH(Me)COOH$, $CH_2CONH_2$, $CH_2CONHNH_2$, or COOH.

Alternatively preferably, Q is

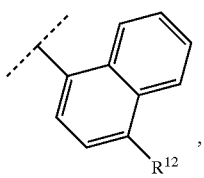

wherein preferably, $R^{12}$ is $(C_{1-6})$alkyl, or $(C_{2-4})$alkenyl, said alkyl or alkenyl being optionally substituted with $R^{13}$ wherein $R^{13}$ is selected from the group consisting of:

a) COOH;
b) $CONHNH_2$; and
c) $CONHSO_2CH_3$;

or $R^{12}$ is:

a) $NHCO(C_{1-6})$alkyl-COOH;
b) $NHSO_2CH_3$ or $NHSO_2CF_3$;
c) COOH; or
d) $SO_2NH_2$, $SO_2NHCOCH_3$, or $SO_2NHCH_2COOH$.

More preferably, $R^{12}$ is $CH_2COOH$, $(CH_2)_2COOH$, $CH_2CH(Me)COOH$, $CH_2CH_2CONHNH_2$, $CH_2CONHSO_2Me$, COOH, $NHCO(CH_2)_2COOH$, $NHCOCH_2C(Me)_2COOH$, $NHSO_2CF_3$, $NHSO_2Me$, $SO_2NH_2$, $SO_2NHAc$, or $SO_2NHCH_2COOH$.

Even more preferably, $R^{12}$ is

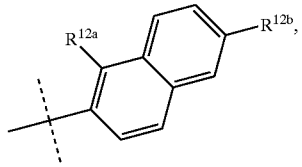

$NHSO_2Me$, $SO_2NH_2$, $SO_2NHCH_2COOH$, or $(CH_2)_2COOH$.

Most preferably, $R^{12}$ is $NHSO_2Me$, $SO_2NH_2$, $SO_2NHCH_2COOH$, or $(CH_2)_2COOH$.

Alternatively preferably, Q is

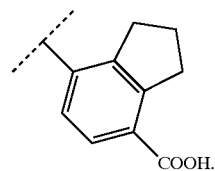

wherein preferably $R^{12b}$ is $(C_{1-6})$alkyl substituted with $R^{13}$ wherein $R^{13}$ is selected from the group consisting of:

a) COOH; and
b) $CONHNH_2$;

or $R^{12b}$ is:

a) COOH;
b) $CONHNH_2$ or $CONHC(Me)_2COOH$;

and preferably $R^{12a}$ is H or $CH_3$.

More preferably, $R^{12b}$ is $CH_2COOH$ and more preferably, $R^{12a}$ is $CH_3$.

Alternatively preferably, Q is

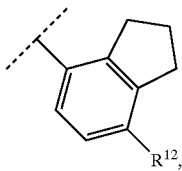

Alternatively preferably, Q is

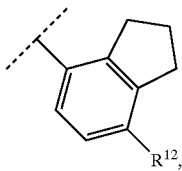

wherein preferably $R^{12}$ is $(C_{1-6})$alkyl substituted with COOH or $R^{12}$ is COOH.

More preferably, $R^{12}$ is $CH_2COOH$, $CH_2CH_2COOH$ or COOH.

Alternatively preferably, Q is

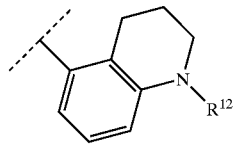

wherein preferably $R^{12}$ is $CH_2COOH$ or $COCH_2COOH$.

Alternatively preferably, Q is

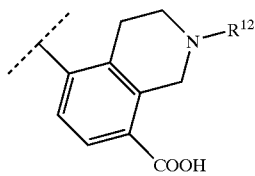

wherein preferably, $R^{12}$ is a) $COCH_3$;
b) $COO(C_{1-6})$alkyl;
c) CONHEt, $CONMe_2$; or
d) $SO_2Me$ or $SO_2N(CH_3)_2$.

More preferably, $R^{12}$ is COMe, $CONMe_2$, COOMe, COO$^t$BU, $SO_2Me$, or $SO_2NMe_2$.

Most preferably, $R^{12}$ is $CONMe_2$, COOMe, COO$^t$BU, or $SO_2NMe_2$.

Specific Embodiments

Included within the scope of this invention are all compounds of formula I as presented in Tables 1 to 7.

The compounds of formula I are effective inhibitors of wild type HIV as well as inhibiting the double mutant enzyme K103N/Y181C. The compounds of the invention may also inhibit the single mutant enzymes V106A, Y188L, K103N, Y181C, P236L and G190A. The compounds may also inhibit other double mutant enzymes including K103N/P225H, K103N/V108I and K103N/L100I.

The compounds of formula I possess inhibitory activity against HIV-1 replication. When administered in suitable dosage forms, they are useful in the treatment of AIDS, ARC and related disorders associated with HIV-1 infection. Another aspect of the invention, therefore, is a method for treating HIV-1 infection which comprises administering to a human being, infected by HIV-1, a therapeutically effective amount of a novel compound of formula I, as described above. Whether it is termed treatment or prophylaxis, the compounds may also be used to prevent perinatal transmission of HIV-1 from mother to baby, by administration to the mother before giving birth.

The compounds of formula I may be administered in single or divided doses by the oral, parenteral or topical routes. A suitable oral dosage for a compound of formula I would be in the range of about 0.5 mg to 3 g per day. A preferred oral dosage for a compound of formula I would be in the range of about 100 mg to 800 mg per day for a patient weighing 70 kg. In parenteral formulations, a suitable dosage unit may contain from 0.1 to 250 mg of said compounds, preferably 1 mg to 200 mg, whereas for topical administration, formulations containing 0.01 to 1% active ingredient are preferred. It should be understood, however, that the dosage administration from patient to patient would vary. The dosage for any particular patient will depend upon the clinician's judgement, who will use as criteria for fixing a proper dosage the size and condition of the patient as well as the patient's response to the drug.

When the compounds of the present invention are to be administered by the oral route, they may be administered as medicaments in the form of pharmaceutical preparations that contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The compounds of formula I can be used in combination with an antiretroviral drug known to one skilled in the art, as a combined preparation useful for simultaneous, separate or sequential administration for treating or preventing HIV infection in an individual. Examples of antiretroviral drugs that may be used in combination therapy with compounds of formula I, include but are not limited to, NRTIs (such as AZT), NNRTI's (such as Nevirapine), reverse transcriptase inhibitors (such as zidovudine and abacavir), CCR5 antagonists (such as TAK-779), CXCR4 antagonists (such as AMD-3100), integrase inhibitors, viral fusion inhibitors (such as T-20), antifungal or antibacterial agents (such as fluconazole), compounds of the TIBO (tetrahydro-imidazo [4,5,1-jk][1,4]-benzodiazepine-2(1H)-one and thione)-type, compounds of the α-APA (α-anilino phenyl acetamide)-type, TAT inhibitors, protease inhibitors (such as Ritanovir), immunomodulating agents (such as Levamisole) and investigational drugs (such as DMP-450 or DPC-083). Moreover, a compound of formula I can be used with another compound of formula I.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula I can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention may be administerable by suppository.

Methodology and Synthesis

Exemplary reaction schemes, disclosed in WO 01/96338A1, the contents of which are incorporated herein by reference, show the many synthetic routes to the tricyclic compounds illustrated hereinafter. The compounds of the present invention may be made using the skills of a synthetic organic chemist. Exemplary reaction schemes are illustrated in Schemes 1 to 4. Substituents $R^2$, $R^4$, $R^5$, $R^{11}$, and $R^{12}$ are as defined herein.

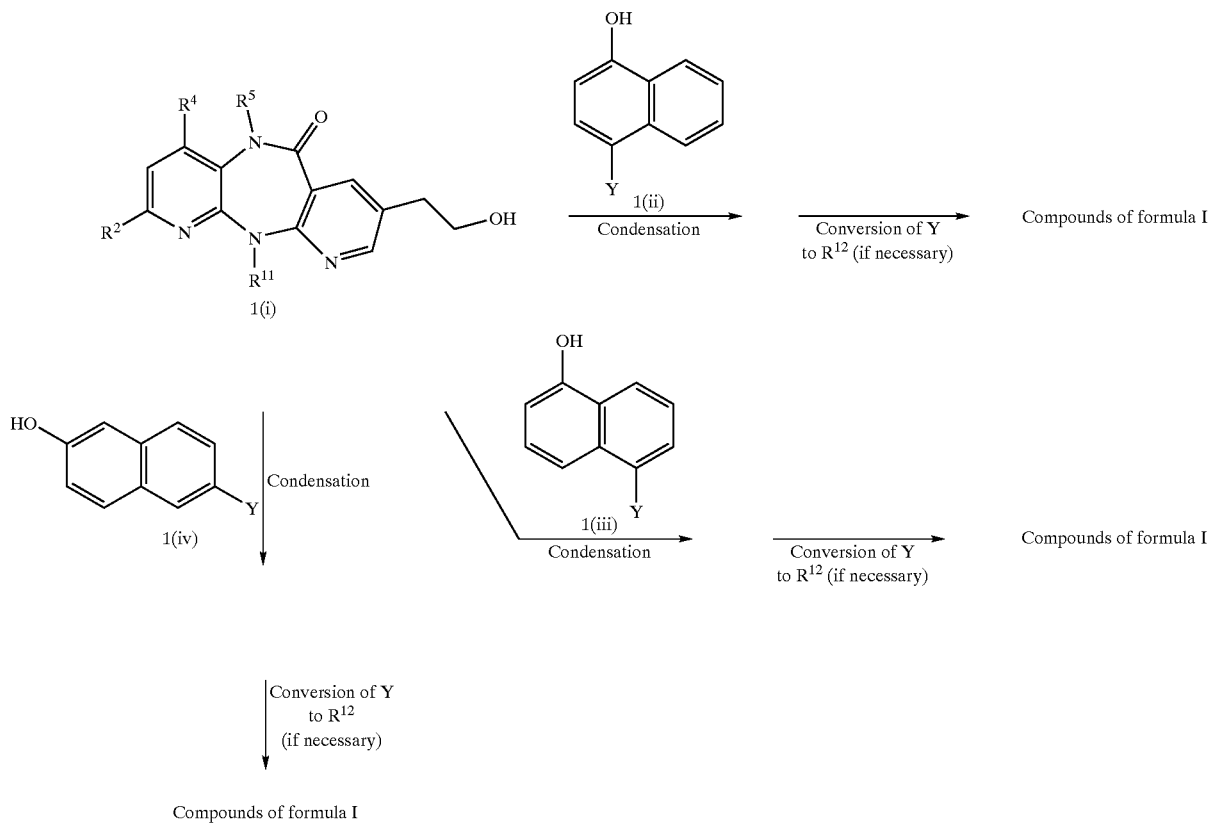

Scheme 1

Introduction of the naphthyl nucleus

Briefly, using a Mitsunobu-type reaction, naphthyl derivatives 1(ii), 1(iii) or 1(iv) when Y is $R^{12}$ with the exception of COOH, are condensed with 1(i) to produce compounds of formula I. Alternatively, when Y is a $R^{12}$ group precursor, for example $COOCH_3$, a Mitsunobu-type reaction can be used to condense 1(iv) or 1(iii) with 1(i), and thereafter Y can be chemically converted into $R^{12}$ substituents, for example by saponification of $COOCH_3$ to give COOH, thereby giving compounds of formula I. Other methods of condensation to produce the ether linkage in compounds of formula I are also contemplated, for example an $S_N2$ displacement of a suitably derivatized primary alcohol in 1(i) by 1(ii), 1(iii) or 1(iv).

Scheme 2

Alternative introduction of the naphthyl nucleus

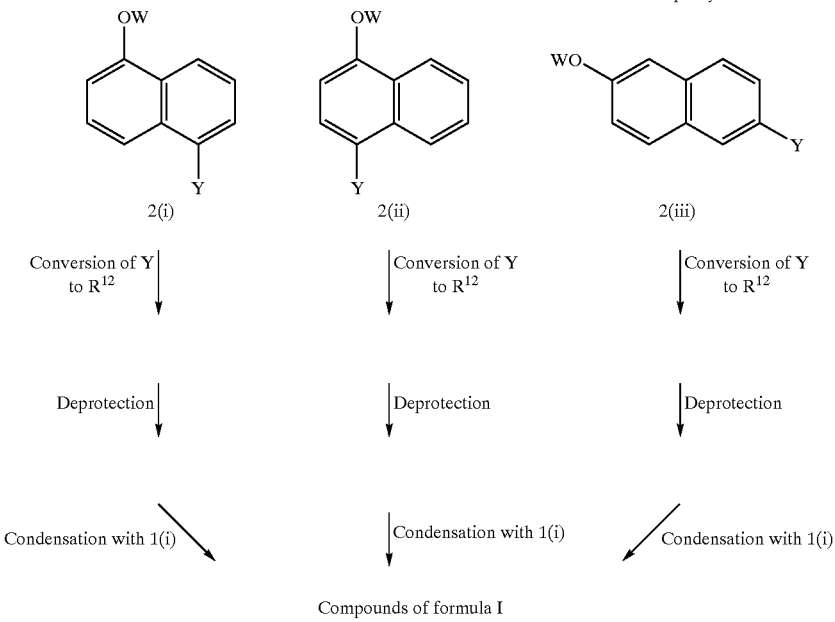

Referring to Scheme 2 above, naphthyl derivatives 2(i), 2(ii), and 2(iii), in which Y is a precursor of $R^{12}$, for example $COOCH_3$, and W is a hydroxyl-protecting group, Y is chemically converted to $R^{12}$, for example by reacting $COOCH_3$ with hydrazine to give $CONHNH_2$. Removal of W using art-recognized chemistry (see "Protective Groups in Organic Synthesis", Theodora W. Greene and Peter G. M. Wuts, second edition, 1991) produces a phenolic derivative, which thereafter is condensed with 1(i) using a Mitsunobu-type condensation, to produce compounds of formula I.

Referring to Scheme 3 above, naphthyl derivatives 3(i), 3(ii), and 3(iii), where Y is a precursor of $R^{12}$, for example $COOCH_3$ and W is a hydroxyl-protecting group, W is removed using art-recognized chemistry (see "Protective Groups in Organic Synthesis", Theodora W. Greene and Peter G. M. Wuts, second edition, 1991). This produces a phenolic derivative, which is condensed with 1(i) using a Mitsunobu-type condensation, followed thereafter by a chemical conversion of Y to $R^{12}$ for example saponification of $COOCH_3$ to give $COOH$, to produce compounds of formula I.

Scheme 3

Alternative introduction of the naphthyl nucleus

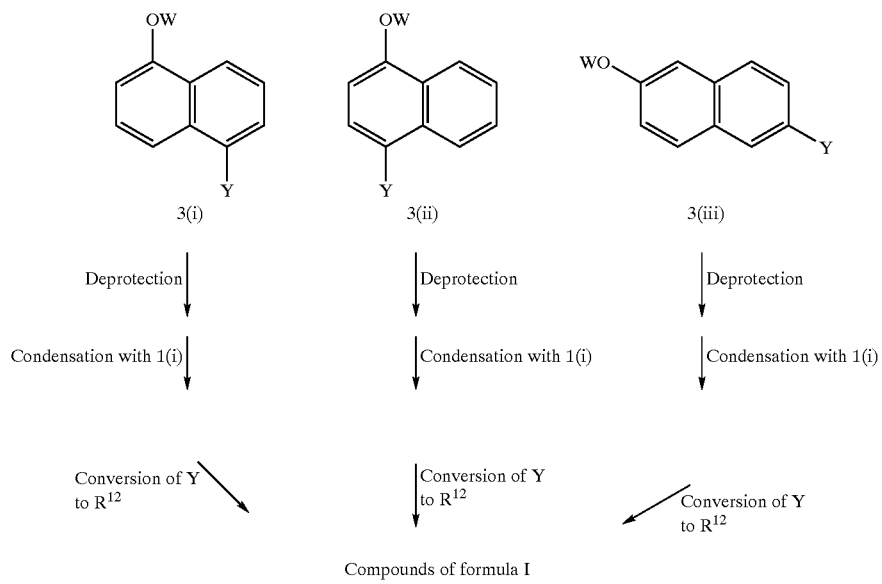

Scheme 4

Introduction of fused aryl-cycloalkyl or fused aryl-heterocycle

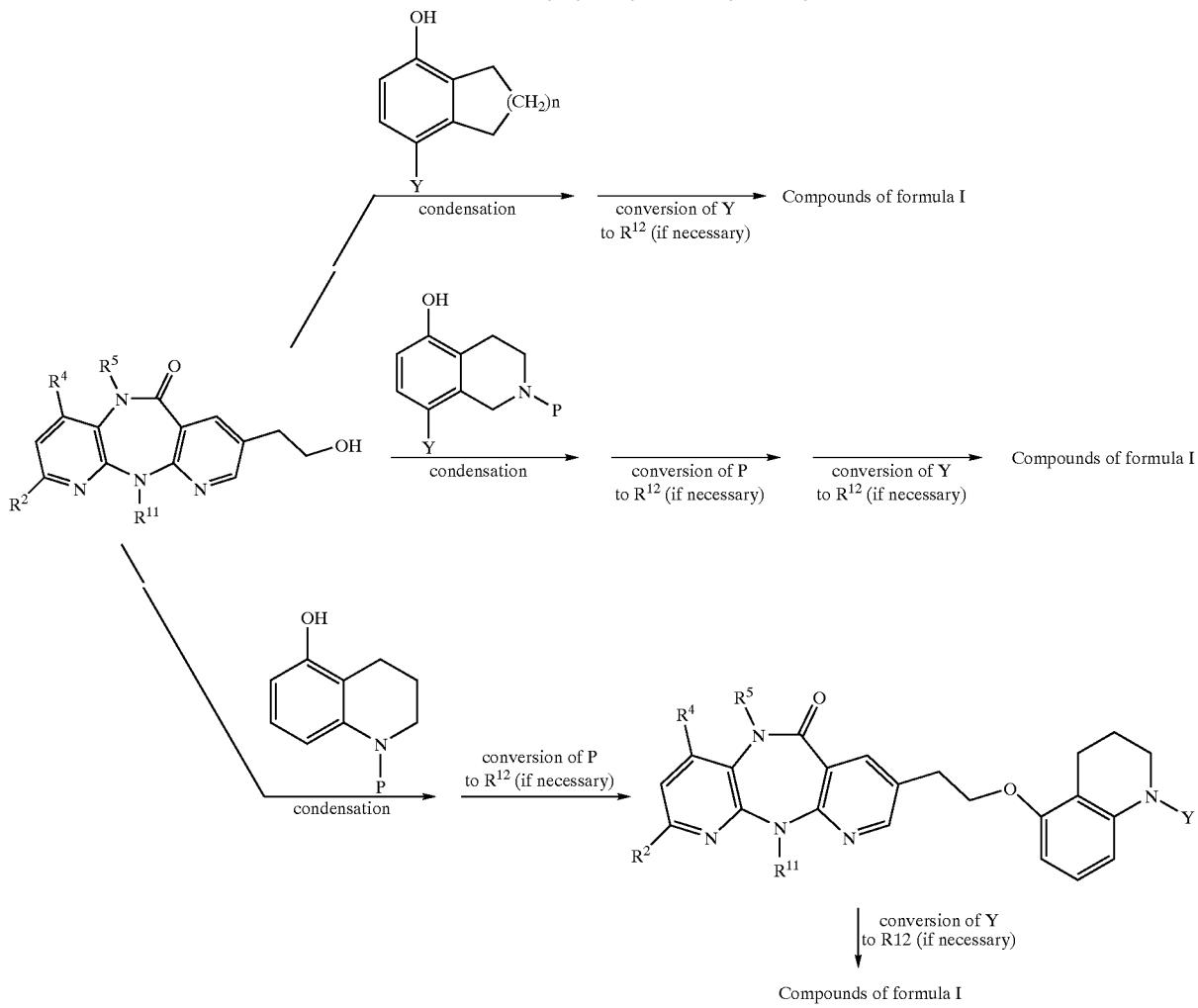

As stated before, the compounds provided by the invention inhibit the enzymatic activity of HIV-1 RT. Based upon testing of these compounds, as described below, it is known that they inhibit the RNA-dependent DNA polymerase activity of HIV-1 RT. It is known (data not shown) that they also inhibit the DNA-dependent DNA polymerase activity of HIV-1 RT. Utilising the Reverse Transcriptase (RT) Assay described below, compounds can be tested for their ability to inhibit the RNA-dependent DNA polymerase activity of HIV-1 RT. Certain specific compounds described in the Examples which appear below, were so tested. The results of this testing appear in Table 4 as $IC_{50}$ (nM) and Table 5 as $EC_{50}$ (nM).

EXAMPLES

The present invention is illustrated in further detail by the following non-limiting examples. All reactions were performed in a nitrogen or argon atmosphere unless otherwise stated. Temperatures are given in degrees Celsius. Solution percentages or ratios express a volume to volume relationship, unless stated otherwise. Abbreviations or symbols used herein include:

Bn: benzyl;
DEAD: diethyl azodicarboxylate;
DIAD: diisopropyl azodicarboxylate;
DIEA: diisopropylethylamine;
DMAP: 4-(dimethylamino)pyridine;
DMSO: dimethylsulfoxide;
DMF: dimethylformamide;
DCC: dicyclohexylcarbodiimide;
DPPP: 1,3-bis (diphenylphosphino) propane
ES MS: electron spray mass spectrometry;
Et: ethyl;
EtOH: ethanol;
EtOAc: ethyl acetate;
Et$_2$O: diethyl ether;
HPLC: high performance liquid chromatography;
iPr: isopropyl;
Me: methyl;
MeOH: methanol;

MeCN: acetonitrile;
NBS: N-bromosuccinimide;
Ph: phenyl;
TBE: tris-borate-EDTA;
TBTU: 2-(1H-benzotriazol-1-yl)-N,N,N',N'-tetramethyluronium tetrafluoroborate;
TFA: trifluoroacetic acid;
THF: tetrahydrofuran;
PFU: plaque-forming units;
DEPC: diethyl pyrocarbonate;
DTT: dithiothreitol;
EDTA: ethylenediaminetetraacetate;
UMP: uridine 5'-monophosphate;
UTP: uridine 5'-triphosphate;
MES: 2-(n-morpholino)ethanesulfonic acid;
SDS-PAGE: sodium dodecyl sulfate-polyacrylamide gel electrophoresis;
MWCO: molecular weight cut-off;
Bis-Tris Propane: 1,3-Bis{tris(hydroxymethyl)-methylamino}propane;
GSH: reduced glutathione;
OBG: n-Octyl-β-D-glucoside.

Syntheses

The following examples illustrate methods for preparing compounds of the invention.

Example 1

(Entry 1006)

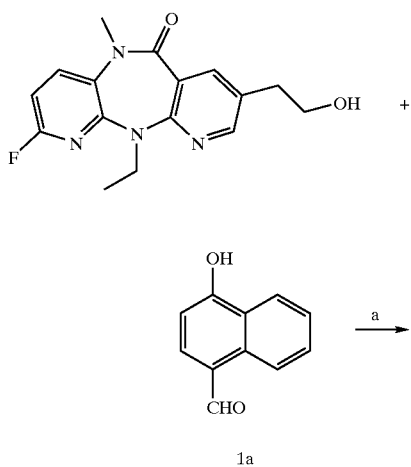

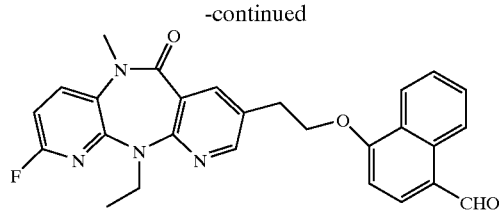

1b

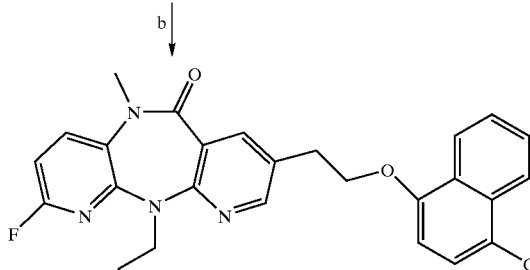

Compound 1006

Step a:

A solution of DIAD (38 µL, 0.2 mmol) in THF (1 mL) was added dropwise to a solution of 5,11-dihydro-11-ethyl-2-fluoro-5-methyl-8-(2-propenyl)-6H-dipyrido[3,2-b:2',3'-e][1,4]diazepin-6-one (45.4 mg, 0.15 mmol), Ph₃P (51 mg, 0.2 mmol) and phenol 1a (34 mg, 0.2 mmol) in THF (5 mL) at room temperature. The mixture was stirred for 1 h then concentrated under reduced pressure. The residue was purified by flash chromatography (hexane/EtOAc; 50/50) to give compound 1b (41.3 mg, 59% yield) as a white solid.

Step b:

To a solution of 1b (32 mg, 0.07 mmol) and silver nitrate (25 mg, 0.14 mmol) in EtOH (2 mL), and THF (2 mL) was added dropwise a solution of 5N NaOH (0.06 mL) in EtOH (0.5 mL). The reaction was stirred at room temperature overnight. After addition of 1N HCl (1 mL), the mixture was concentrated under reduced pressure. The residue was diluted with EtOAc, washed with water, brine, dried over MgSO₄, filtered, and concentrated. The resulting solid was triturated with hexane to give compound 1006 (21 mg, 62% yield) as a white solid.

Example 2

(Entry 1009)

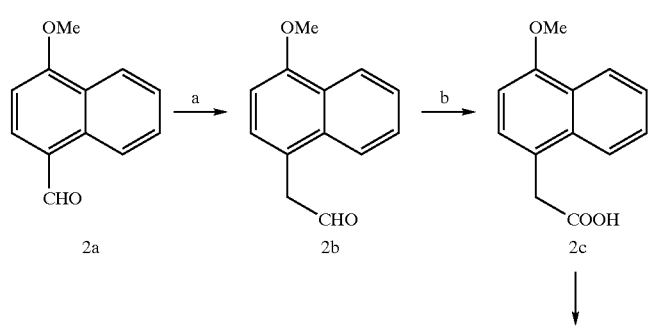

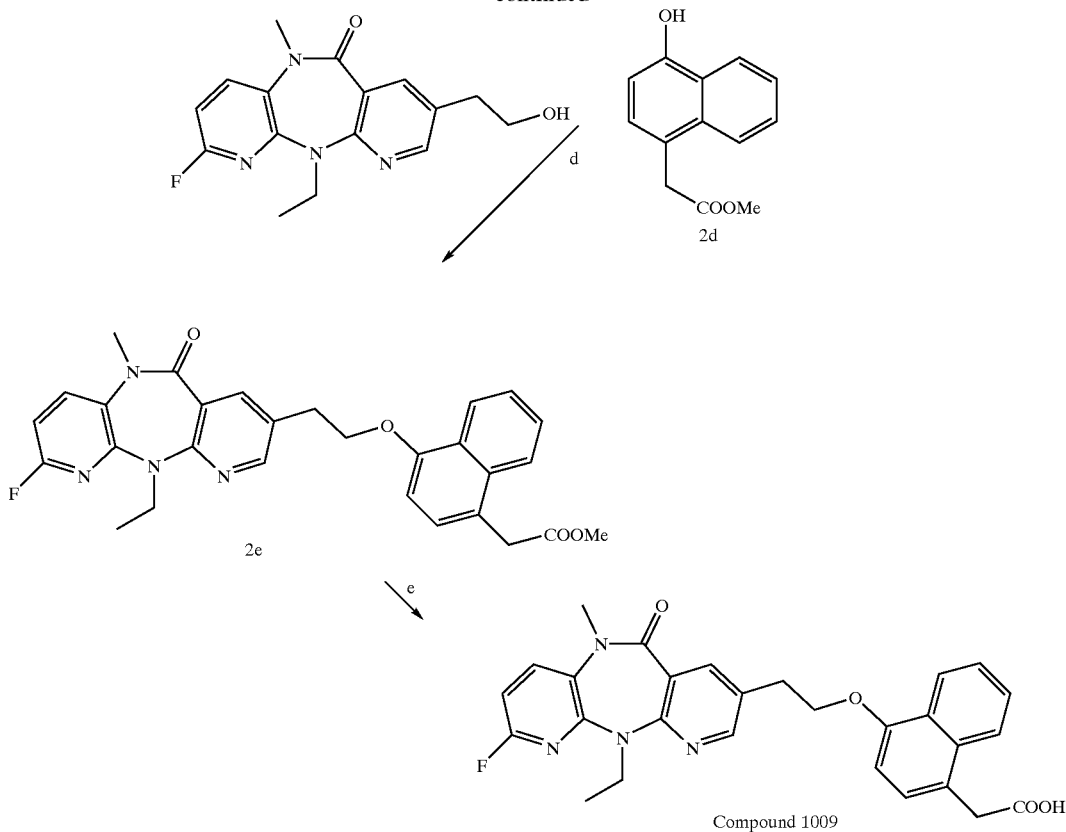

Step a:

A solution of n-butyllithium (2.5 M, 2.8 mL, 7.17 mmol) in hexane was added drop-wise to a stirred solution of methoxymethyltriphenylphosphonium chloride (2.5 g, 7.17 mmol) in THF (15 mL). After 2 h at room temperature, solid aldehyde 2a (667.6 mg, 3.6 mmol) was added and stirring was continued for 20 h. The reaction mixture was diluted with Et$_2$O and successively washed with water and brine, dried (MgSO$_4$), filtered and concentrated. The residue was diluted in THF (15 mL) and HCl (6N, 5 mL) was added. After 20 h at room temperature, the reaction was diluted in Et$_2$O and layers were separated. The organic layer was successively washed with water and brine, dried (MgSO$_4$), filtered and concentrated to dryness. The residue was purified by flash chromatography (hexane/EtOAc; 90/10) to give compound 2b (487.7 mg, 67% yield) as a yellow gum.

Step b:

Using the oxidation procedure described in Example 1 step b, aldehyde 2b(1 g, 5.06 mmol) gave acid 2c (839.4 mg, 77% yield) as an orange solid, which was used without purification.

Step c:

To a solution of acid 2c (839 mg, (3.88 mmol) in CH$_2$Cl$_2$ (6 mL) was added a 1M solution of BBr$_3$ in CH$_2$Cl$_2$ (20 mL). After 2 h at room temperature, the reaction mixture was cooled to 0° C. and MeOH (10 mL) was added. The reaction mixture was stirred at room temperature overnight then was concentrated under reduced pressure. The residue was diluted with EtOAc and successively washed with saturated aqueous NaHCO$_3$ solution, water and brine, dried (MgSO$_4$), filtered and concentrated to dryness. The residue was purified by flash chromatography (hexane/EtOAc; 80/20) to give phenol 2d (485 mg, 50% yield) as a brown solid.

Step d:

Following the procedure described in Example 1, 5,11-dihydro-11-ethyl-2-fluoro-5-methyl-8-(2-propenyl)-6H-dipyrido[3,2-b:2 ',3'-e][1,4]diazepin-6-one (99.4 mg, 0.31 mmol) and phenol 2d (68 mg, 0.31 mmol) gave, after purification, compound 2e (114.5 mg, 71% yield) as a white foam.

Step e:

To a solution of ester 2e (112.5 mg, 0.22 mmol) in a mixture of THF (8 mL) and water (2 mL) was added LiOH (36.7 mg, 87 mmol). After 1.5 h at room temperature, the reaction mixture was concentrated to 1/5 the volume and 1N HCl (2 mL) was added. The mixture was extracted with EtOAc. The organic layer was washed with water and brine, dried (MgSO$_4$), filtered and concentrated to dryness to give compound 1009 (70 mg, 64% yield) as a white solid.

Example 3

(Entry 1016)

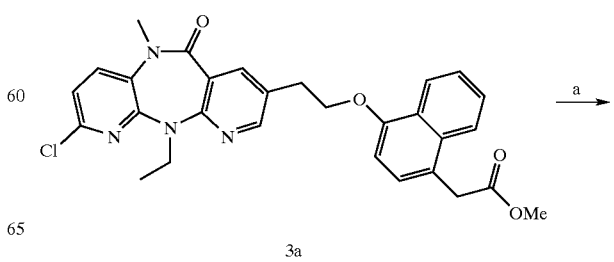

3a

-continued

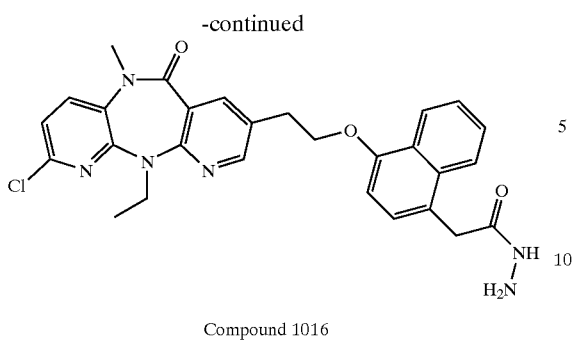

Compound 1016

Step a:
Compound 3a was obtained from Mitsunobu reaction of 2-chloro-5,11-dihydro-11-ethyl-8-(2-hydroxyethyl)-5-methyl-6H-dipyrido[3,2-b:2',3'-e][1,4]diazepin-6-one and phenol 2d (Example 2) following the same procedure as in Example 1. A solution of 3a(46 mg, 0.09 mmol) and hydrazine (0.2 mL) in THF (0.5 mL) and EtOH (3 mL) was heated to 85° C. overnight. After cooling to room temperature, the precipitate was filtered, washed with EtOH, and dried to give the desired compound 1016 as a white solid (23 mg, 43% yield).

Example 4

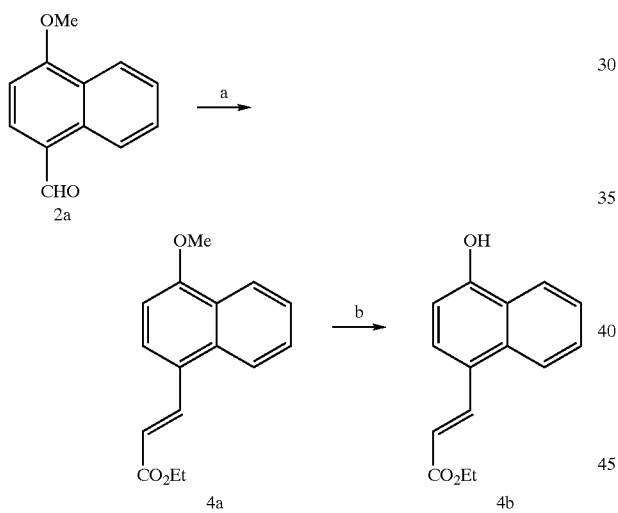

Step a:
To a cooled solution (−60° C.) under $N_2$ of triethyl phosphonoacetate (2.13 mL, 10.7 mmol) in THF (35 mL) was added over 5 min a 2.5M solution of n-BuLi in hexane (4.3 mL, 10.7 mmol). A solution of 4-methoxynaphthaldehyde 2a(2.0 g, 10.74 mmol) in THF (10 mL) was added dropwise and the reaction mixture was stirred for 45 min at −60° C. The reaction mixture was allowed to warm to room temperature. After 30 min, the reaction was concentrated under reduced pressure and the residue was taken up in $Et_2O$. The organic layer was washed with $H_2O$ and brine, dried ($MgSO_4$), filtered and evaporated to dryness to give 4a(2.77 g, 100% yield) as a yellow syrup which solidified over time.

Step b:
To a solution of 4a(2.0 g, 7.81 mmol) in DMF (20 mL), was added NaSMe (710 mg, 10.1 mmol). The resulting solution was brought to reflux for 90 min. The reaction mixture was cooled to room temperature, EtOH (15 mL) was added, and stirring was continued for 30 min. The reaction was poured into 1N HCl (100 mL) followed by addition of $H_2O$ (350 mL). The mixture was extracted twice with EtOAc. The combined organic layers were washed twice with 1N HCl, brine, dried ($MgSO_4$), filtered and concentrated to dryness. The residue was purified by flash chromatography (hexane/EtOAc; 70/30) to provide 4b(1.42 g, 75% yield) as a light yellow solid.

Example 5

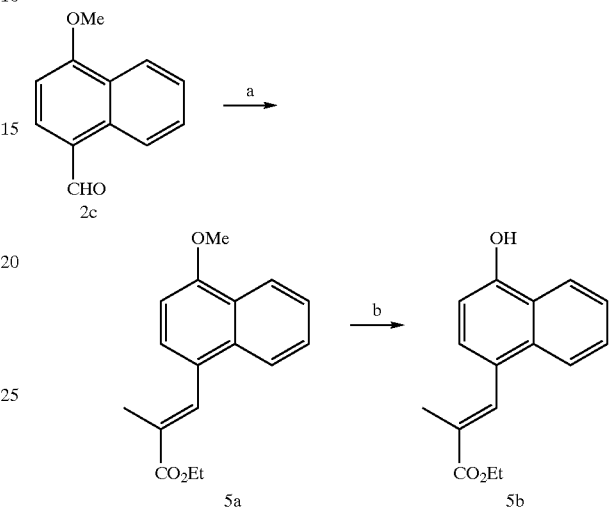

Step a, b:
Following the 2 step procedure described in Example 4, aldehyde 2c and triethyl-2-phosphonopropionate provided compound 5b in 43% overall yield.

Synthesis of Compounds 1028 and 1035:
Using the procedure of the Mitsunobu reaction described in Example 1 and the hydrolysis procedure described in Example 2, intermediates 4b and 5b were transformed in compounds 1028 and 1035 respectively.

Example 6
(Entry 1050)

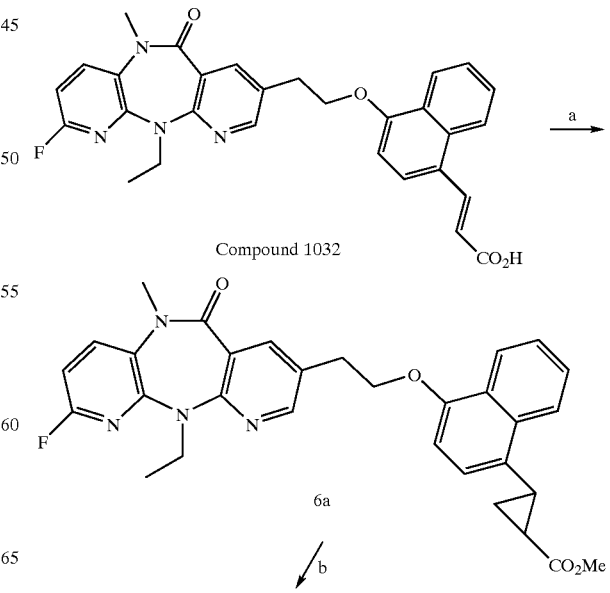

-continued

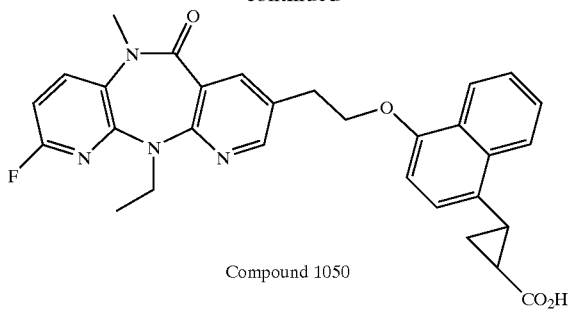

Compound 1050

Step a:

To a suspension of 1032 (26 mg, 0.05 mmol) in Et$_2$O was added a CH$_2$N$_2$ ethereal solution (0.7 M, 15 mL). After 30 min, the reaction mixture was cooled to 0° C. and Pd(OAc)$_2$ (2 mg) was added. The reaction was stirred at 0° C. for 1 h, the excess CH$_2$N$_2$ was quenched by the addition of silica gel and the reaction mixture was concentrated to dryness. The residue was purified by flash chromatography (hexane/EtOAc; 70/30) to give 6a(9 mg, 33% yield).

Step b:

Following the procedure described in Example 2, ester 6a gave compound 1050 isolated as a white solid.

Example 7

(Entry 2001)

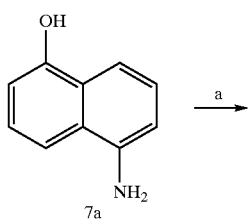

7a

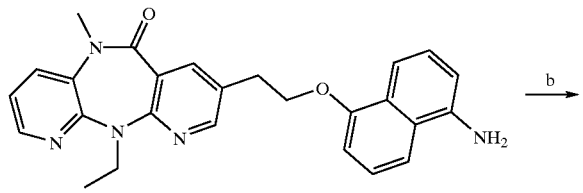

7b

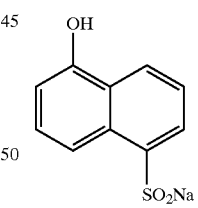

Compound 2001

Step a:

Following the procedure described in Example 1, but using DEAD instead of DIAD, 5-amino-1-naphthol 7a and 5,11-dihydro-11-ethyl-8-(2-hydroxyethyl)-5-methyl-6H-dipyrido[3,2-b:2',3'-e][1,4]diazepin-6-one gave compound 7b in 76% yield as a purple gum.

Step b:

To a solution of 7b (42 mg, 0.09 mmol) in acetone (1 mL) was added pyridine (0.3 mL) and methanesulfonyl chloride (0.1 mL). After 3 h at room temperature, the reaction mixture was concentrated to dryness. The residue was purified on reverse phase HPLC (CombiPrep ADS-AQ 50×20 mm, 5μ, 120 Å) using a gradient of MeCN/H$_2$O containing TFA (0.06%) to give compound 2001 (13.4 mg, 25% yield) as a tan solid.

Example 8

(Entry 2004)

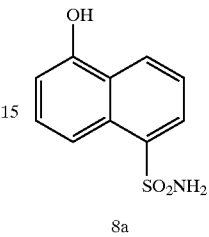

8a

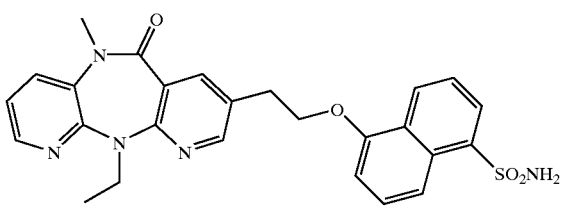

Compound 2004

Step a:

Following the procedure described in Example 1, but using DEAD instead of DIAD, phenol 8a and 5,11-dihydro-11-ethyl-8-(2-hydroxyethyl)-5-methyl-6H-dipyrido[3,2-b:2',3'-e][1,4]diazepin-6-one gave compound 2004 in 14% yield as white solid.

Example 9

(Entry 2008)

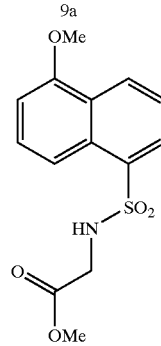
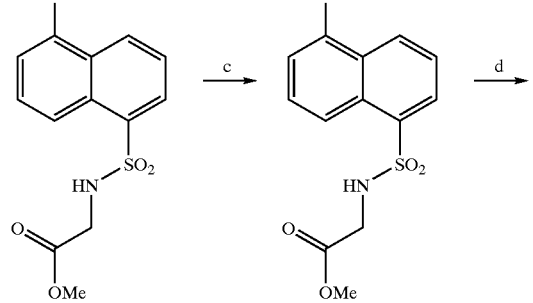

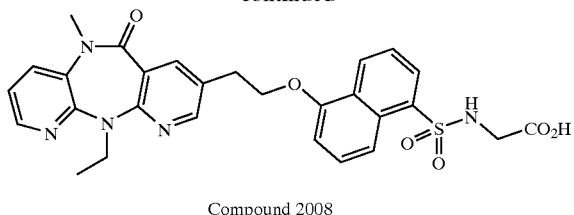

Compound 2008

Step a:

To a solution of 1-naphthol-5-sulfonic acid sodium salt 9a(3.5 g, 14.2 mmol) in H₂O (10 mL) was added 5M NaOH (3.3 ml, 16.3 mmol) and dimethyl sulfate (1.4 ml, 14.9 mmol). The resulting solution was heated to reflux for 3 h, then cooled to 5° C. The precipitate was filtered and dried under reduced pressure for two days providing 9b (2.6 g, 70% yield).

Step b:

To a solution of 9b (400 mg, 1.5 mmol) in $SOCl_2$ (5 mL) and $CH_2Cl_2$ (10 mL), was added DMF (1 drop). The resulting mixture was heated to reflux for 16 h, then was evaporated to dryness. The residue was dissolved in hexane/EtOAc (1/1) and filtered through a short silica plug. The filtrate was concentrated under reduced pressure to provide the corresponding sulfonyl chloride (300 mg, 76%). A solution of the sulfonyl chloride intermediate (270 mg, 1.1 mmol) in $CHCl_3$ (10 mL) was added to a solution of $iPr_2NEt$ (411 μL, 2.3 mmol) and glycine methyl ester hydrochloride (143 mg, 1.2 mmol) in $CHCl_3$ (5 mL). After 18 h at room temperature, the reaction mixture was concentrated to dryness. The residue was taken up in EtOAc, washed successively with H₂O, 1N HCl, and brine, dried (MgSO₄), filtered and concentrated. The residue was purified by flash chromatography (hexane/EtOAc; 60/40) to afford compound 9c (28 mg, 86% yield).

Step c:

To a solution of 9c (150 mg, 0.48 mmol) in $CH_2Cl_2$ (15 mL) was added a 1M solution of $BBr_3$ in $CH_2Cl_2$ (2.5 ml, 2.5 mmol). After 15 hr at room temperature, the reaction was quenched by careful addition of H₂O. The mixture was diluted with EtOAc, washed with H₂O and brine, dried (MgSO₄), filtered and concentrated to dryness. The residue was taken up in $CH_2Cl_2$ (6 mL) and THF (2 mL) and treated with a $CH_2N_2$ ethereal solution (0.7 M, 1.5 mL). After 30 min, the reaction mixture was quenched by addition of silica gel. The resulting mixture was concentrated to dryness and the residue was purified by flash chromatography (hexane/EtOAc; 50/50) to give compound 9d (63 mg, 44% yield) as a yellow solid.

Step d:

Following the procedure described in Example 1, but using DEAD instead of DIAD, phenol 9d and 5,11-dihydro-11-ethyl-8-(2-hydroxyethyl)-5-methyl-6H-dipyrido[3,2-b:2',3'-e][1,4]diazepin-6-one gave after saponification of the ester, as described in Example 2, step e, compound 2008 as white solid.

Example 10

(Entries 2011 and 2012)

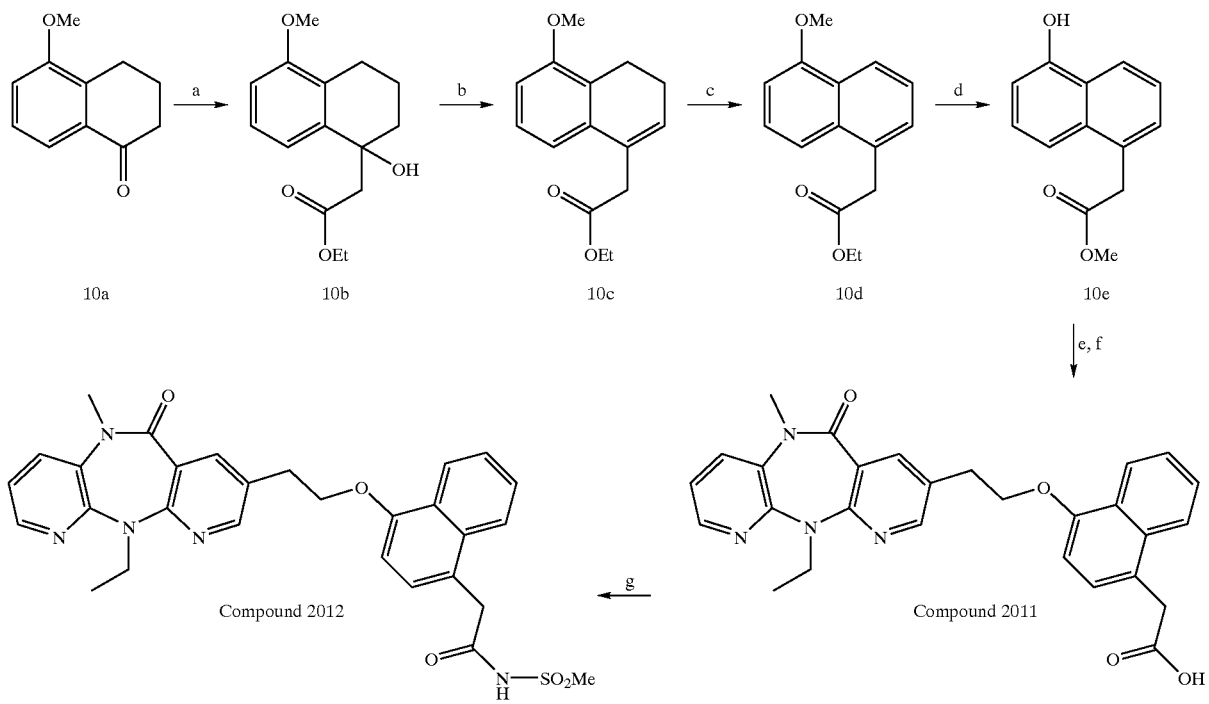

Step a:

To a 1M solution of LiHMDS in THF (30 mL, 30 mmol) at −78° C. was added EtOAc (2.9 ml, 30 mmol), dried overnight with 4A molecular sieves) via syringe pump over 15 min. After 15 min at −78° C., a solution of 5-methoxy-1-tetralone 10a (5.3 g, 30 mmol) in THF (30 ml) was added dropwise over 45 min. The reaction mixture was stirred at −78° C. for 20 min then was quenched with 20% HCl (7.5 mL) and was allowed to warm to room temperature. The mixture was diluted with H₂O, extracted with EtOAc. The combined organic layers were washed with brine, dried (MgSO₄), filtered and concentrated to dryness to give 10b (8.10 g, 100% yield) as a pale yellow solid.

Step b:

A solution of 10b (1.65 g, 6.3 mmol) and p-TsOH (250 mg) in benzene (10 mL) was heated to reflux for 30 min. The reaction mixture was diluted with EtOAc, washed successively with saturated aqueous $NaHCO_3$, and brine, dried ($MgSO_4$), filtered and concentrated to dryness to give compound 10c (1.6 g, 100% yield) as a mixture of two compounds in which the double bond is endo and exocyclic.

Step c:

To a solution of 10c (0.45 g, 1.8 mmol) in diglyme (10 mL) was added Pd/C (10%, 230 mg) and the resulting mixture was heated to reflux for 2 h. After cooling to room temperature, the reaction mixture was diluted with $Et_2O$, filtered and concentrated to dryness. A mixture of two compounds 10d was obtained (450 mg) and was used as such in the subsequent reaction.

Step d:

Following the demethylation procedure described in Example 4, compound 10d gave compound 10e in 19% yield.

Step e and f:

Using a procedure similar to the one described in Example 1, followed by the hydrolysis of the resulting ester as described in Example 2, intermediate 10e and 5,11-dihydro-11-ethyl-8-(2-hydroxyethyl)-5-methyl-6H-dipyrido[3,2-b:2',3'-e][1,4]diazepin-6-one were transformed into compound 2011, isolated as a white solid.

Step g:

To a mixture of compound 2011 (31 mg, 0.07 mmole), DMAP (10 mg, 0.08 mmole) and methanesulfonamide (10 mg, 0.1 mmol) in $CH_2Cl_2$ (3 mL) and THF (1 mL) was added DCC (1 M in $CH_2Cl_2$, 86 μL, 0.09 mmol). After stirring for 72 h at room temperature, the reaction mixture was acidified with 1N HCl, and extracted with EtOAc. The organic layer was washed with brine, dried ($MgSO_4$), filtered and concentrated under reduced pressure. The residue was purified on reverse phase HPLC (CombiPrep ADS-AQ, 50×70 mm, 5μ, 120A) using a gradient of $MeCN/H_2O$ containing TFA (0.06%) to provide compound 2012 (7.2 mg, 19% yield).

Example 11

(Entries 3001, 3002, and 3003)

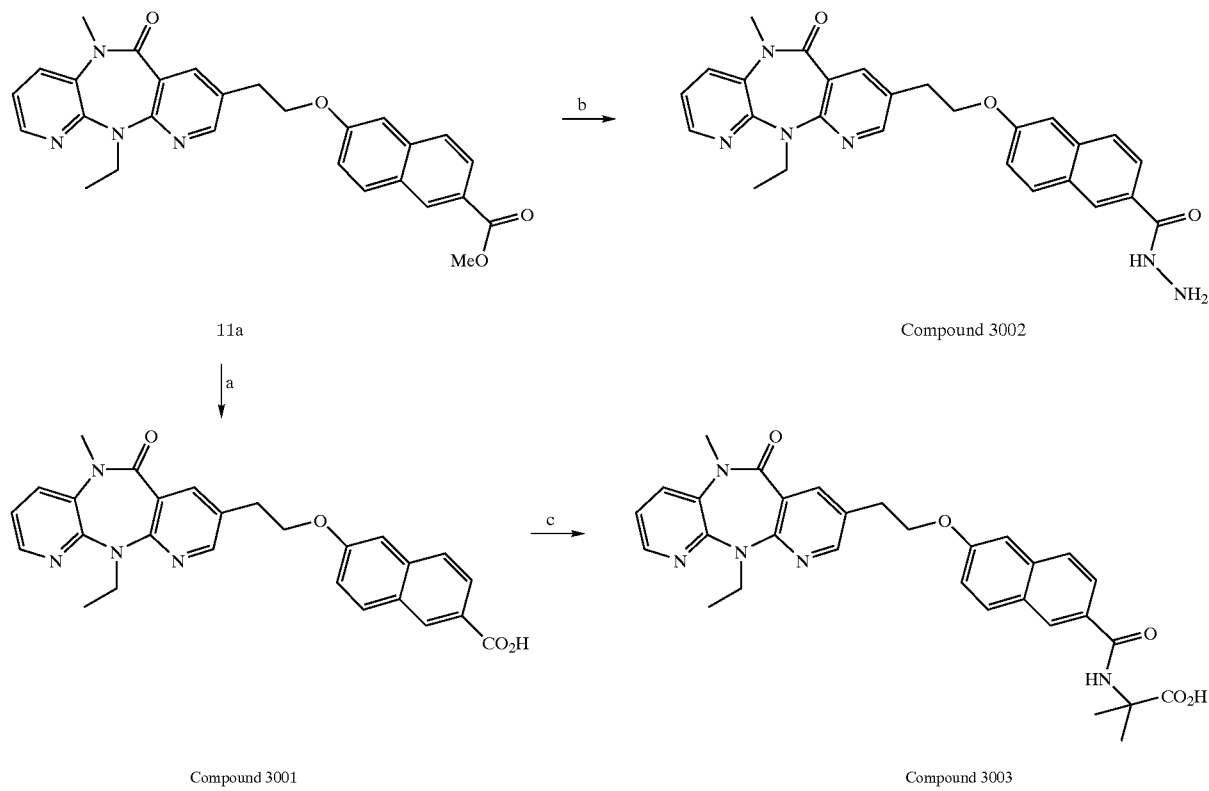

Step a:

Compound 11a was obtained from methyl 6-hydroxy-2-naphtoate and 5,11-dihydro-11-ethyl-8-(2-hydroxyethyl)-5-methyl-6H-dipyrido[3,2-b:2',3'-e][1,4]diazepin-6-one using a procedure similar to the one described in Example 1. Compound 11a was hydrolysed using the procedure described in Example 2 to give compound 3001 (60% yield) as a white solid.

Step b:

Following the procedure described in Example 3, compound 11a gave compound 3002 (73% yield) as a white solid.

Step c:

To a solution of compound 3001 (85 mg, 0.18 mmol) in $CH_2Cl_2$ (9 mL) was added methyl 2-aminoisobutyrate hydrochloride (30.7 mg, 0.2 mmol), TBTU (64 mg, 0.2 mmol) and N-methylmopholine (60 μL, 0.55 mmol). After 16 h at room temperature, the reaction mixture was diluted with EtOAc and the resulting solution was washed successively with 10% aqueous citric acid, water, and brine, dried ($MgSO_4$) filtered and evaporated to dryness. The residue was purified by flash chromatography (hexane/EtOAc; 60/40) to give the coupling product (73.7 mg, 71% yield) as a colorless gum. To a solution of the ester (35 mg, 0.06 mmol) in EtOH (5 mL) was added 1N NaOH (185 μL) and water (1 mL). After stirring for 16 hr at room temperature, the reaction mixture was concentrated to dryness. The residue was diluted with water and acidified with 1N HCl to give a white precipitate. The solid was filtered, washed with water, and dried, to give compound 3003 (24.1 mg, 70% yield).

Example 12

(Entry 4001)

4]diazepin-6-one (74.0 mg, 0.25 mmol), 12d (80.0 mg, 0.30 mmol) and PPh$_3$ (98.0 mg, 0.37 mmol) in THF (4 mL) at 25° C. The reaction mixture was stirred at 25° C. for 16 h. The mixture was concentrated under reduced pressure. The residue was purified by flash chromatography (toluene/EtOAc, 17/3) to give 12e (59 mg, 43% yield) as a white solid.

Step e:

A mixture of 12e (59.0 mg, 0.11 mmol) and 20% Pd(OH)$_2$/C (4.0 mg) in THF (1 mL) and MeOH (4 mL) was stirred under hydrogen (1 atm.) for 1 h. The reaction mixture was filtered and the filtrate was concentrated under reduced pressure. The residue was triturated with MeCN. The resulting solid was dissolved in MeCN and aqueous 0.01 N NaOH

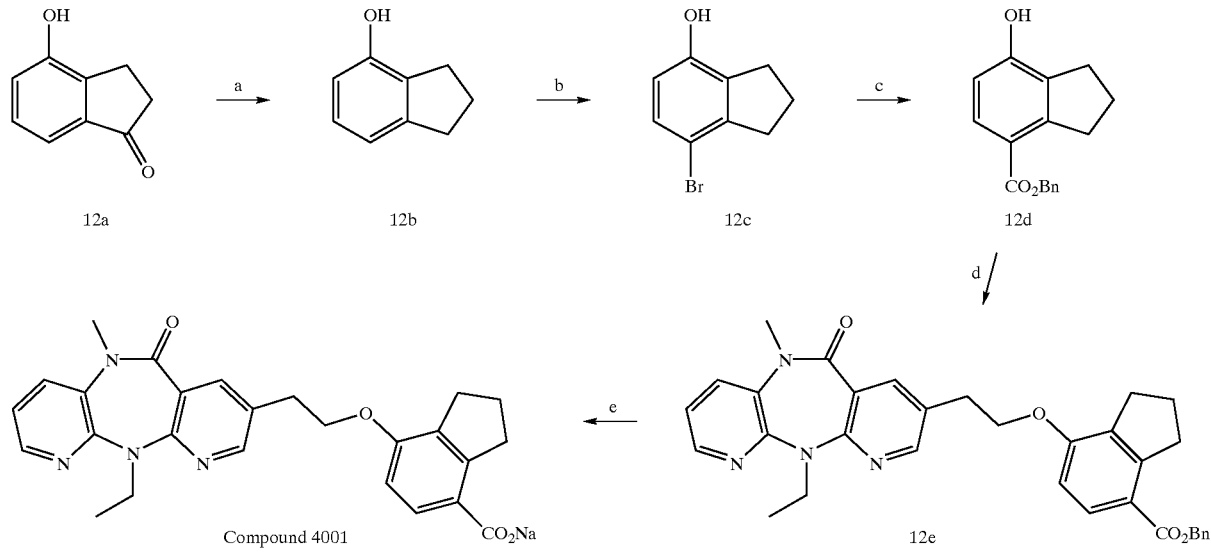

solution (1 equiv., 4.6 mL, 0.046 mmol) was added. The resulting solution was frozen and lyophilized to give 4001 (22 mg, 43% yield) as a white solid.

Step a:

A mixture of 12a (5.35 g, 36.1 mmol) and 20% Pd(OH)$_2$/C (100 mg) in MeOH (80 mL) and THF (20 mL) was stirred at 25° C. under hydrogen (1 atm.) for 24 h. The mixture was filtered and concentrated under reduced pressure to yield 12b (5.10 g, 100% yield).

Step b:

A 2 M solution of Br$_2$ in CCl$_4$ (5.30 mL, 11.0 mmol) was added to a solution of 12b (1.43 g, 10.7 mmol) in CH$_2$Cl$_2$ (40 mL) and the resulting solution was stirred at 25° C. for 1 h. The reaction mixture was concentrated under reduced pressure. The residue was purified by flash chromatography (hexane/EtOAc, 17/3) to give 12c (2.02 g, 89% yield).

Step c:

A solution of 0.8 M sec-BuLi in cyclohexane (7.80 mL, 6.27 mmol) was added dropwise to an ice-cold solution of 12c (607 mg, 2.85 mmol) in THF (20 mL). The reaction mixture was stirred at 0° C. for 1 h. CNCO$_2$Bn (1.00 mL, 6.30 mmol) was next added and the reaction mixture was allowed to warm slowly to 25° C. in 2 h. The reaction mixture was poured into an aqueous 1N HCl solution/brine mixture (1:1) and was extracted with EtOAc (2×). The combined organic layers were dried (MgSO$_4$), filtered and concentrated under reduced pressure. The residue was purified by flash chromatography (hexane/EtOAc, 20/1 to 4/1) to give 12d (157 mg, 20% yield).

Step d:

A solution of DIAD (70 μL, 0.38 mmol) in THF (0.2 mL) was added dropwise to a solution of 5,11-dihydro-11-ethyl-8-(2-hydroxyethyl)-5-methyl-6H-dipyrido[3,2-b:2',3'-e][1, Example 13

(Entry 5001)

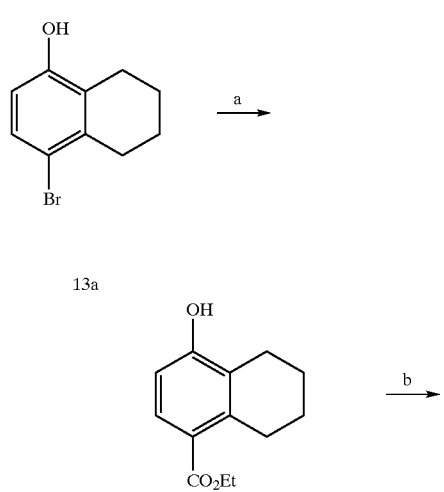

-continued

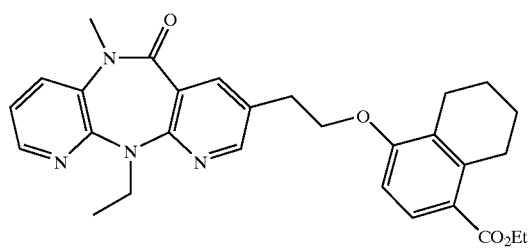

13c

↓ c

Compound 5001

Step a:

A solution of 1.2 M sec-BuLi in cyclohexane (18.0 mL, 21.3 mmol) was added dropwise to an ice-cold solution of 13a (2.20 g, 9.69 mmol) in THF (50 mL). The reaction mixture was stirred at 0° C. for 1 h. CNCO$_2$Et (2.11 mL, 21.3 mmol) was next added and the reaction mixture was allowed to warm slowly to 25° C. and stirred at this temperature for 16 h. The reaction mixture was poured into a mixture of aqueous 1 N HCl solution and brine (1:1). The resulting mixture was extracted with EtOAc (2×). The combined organic layers were dried (MgSO$_4$), filtered and concentrated under reduced pressure. The residue was purified by flash chromatography (hexane/EtOAc, 10/1 to 7/3) to give 13b (462 mg, 22% yield).

Step b:

A solution of DIAD (74 μL, 0.40 mmol) in THF (0.5 mL) was added dropwise to a solution of 5,11-dihydro-11-ethyl-8-(2-hydroxyethyl)-5-methyl-6H-dipyrido[3,2-b:2',3'-e][1,4]diazepin-6-one (80.6 mg, 0.27 mmol), 13b (60.0 mg, 0.27 mmol) and PPh$_3$ (106 mg, 0.40 mmol) in THF (5 mL) at 25° C. The reaction mixture was stirred at 25° C. for 16 h. The mixture was concentrated under reduced pressure. The residue was purified by flash chromatography (first purification: hexane/EtOAc, 17/3 to 7/3, second purification: toluene/EtOAc, 4/1) to give 13c (100 mg, 74% yield) as a white solid.

Step c:

An aqueous 2.5 N NaOH solution (0.7 mL, 1.75 mmol) was added to a solution of 13c (100 mg, 0.20 mmol) in THF (1.5 mL) and MeOH (1.5 mL). The reaction mixture was stirred at 25° C. for 5 h. The mixture was rendered acidic with aqueous 1 N HCl solution and the mixture was concentrated under reduced pressure. Water was added to the residue and the resulting suspension was filtered. The solid washed with Et$_2$O was dissolved in MeCN and treated with aqueous 0.5 M NaOH solution (1 equivalent). The resulting solution was frozen and lyophilized to give compound 5001 (61 mg, 62% yield) as a white solid.

Example 14

(Entry 7003)

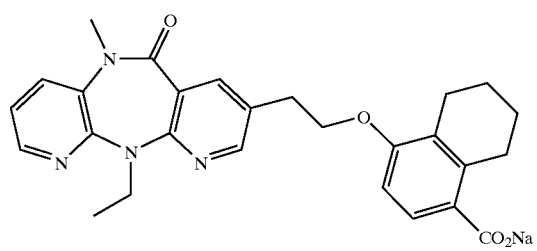

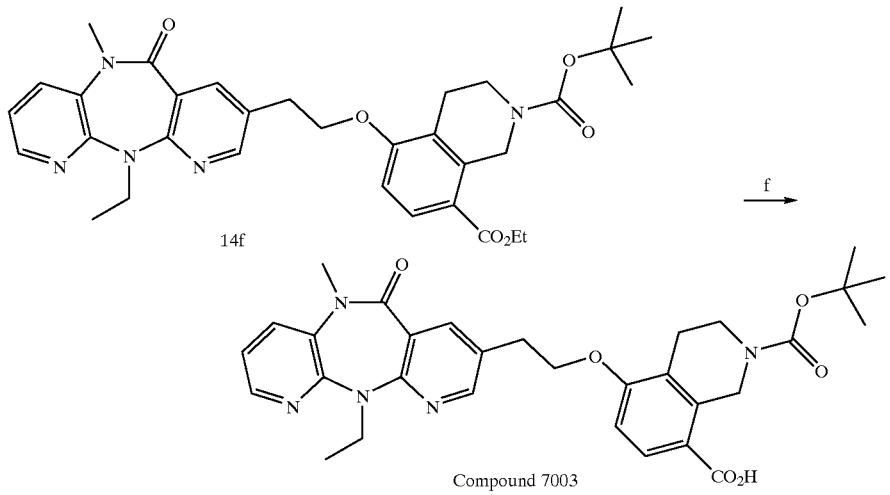

Compound 7003

Step a:

A mixture of 14a(3.17 g, 21.8 mmol), PtO$_2$ hydrate (380 mg) and aqueous 12 N HCl solution (1.5 mL) in EtOH (120 mL) was stirred under hydrogen (50 psi, Parr shaker) for 16 h. The mixture was diluted with CH$_2$Cl$_2$ (100 mL), filtered and concentrated under reduced pressure to give hydrochloride 14b(3.38 g, 83% yield) as a white solid.

Step b:

A solution of 2 M Br$_2$ in CCl$_4$ (9.00 mL, 18.0 mmol) was added to a solution of the hydrochloride salt of 14b(3.18 g, 17.1 mmol) in CH$_2$Cl$_2$ (100 mL). The reaction was stirred at 25° C. for 6 h. The resulting suspension was filtered. The solid was washed with CH$_2$Cl$_2$ and dried to give hydrobromide 14c (5.20 g, 98% yield) as a white solid.

Step c:

A mixture of the hydrobromide salt of 14c (5.56 g, 18.0 mmol), (t-BuOCO)$_2$O (4.15 g, 19.0 mmol) and N-methylmorpholine (4.60 mL, 41.8 mmol) in CH$_2$Cl$_2$ (80 mL) was stirred at 25° C. for 5 h. The reaction mixture was poured into aqueous 0.5 M HCl solution and the resulting mixture was extracted with CH$_2$Cl$_2$. The organic layer was dried (MgSO$_4$), filtered and concentrated under reduced pressure to give 14d (4.36 g, 74% yield).

Step d:

Pd(OAc)$_2$ (299 mg, 1.33 mmol) and DPPP (530 mg, 1.33 mmol) were added to a degassed (argon) solution of 14d (4.36 g, 13.3 mmol) and Et$_3$N (4.05 mL, 29.3 mmol) in DMF (40 mL) and EtOH (20 mL). The mixture was heated to 80° C. for 16 h under a CO atmosphere (1 atm.). The reaction mixture was concentrated under reduced pressure. The residue was partitioned between water and EtOAc. The aqueous layer was extracted with EtOAc. The combined organic layers were washed with water, dried (MgSO$_4$), filtered and concentrated under reduced pressure. The residue was purified by flash chromatography (hexane/EtOAc, 17/3 to 4/1) to give 14e (940 mg, 22% yield) and recovered 14d (1.50 g, 34%).

Step e:

A solution of DIAD (125 μL, 0.68 mmol) in THF (0.5 mL) was added dropwise to a solution of 5,11-dihydro-11-ethyl-8-(2-hydroxyethyl)-5-methyl-6H-dipyrido[3,2-b:2',3'-e][1,4]diazepin-6-one (134 mg, 0.45 mmol), 14e (150 mg, 0.47 mmol) and PPh$_3$ (178 mg, 0.68 mmol) in THF (10 mL) at 25° C. The reaction mixture was stirred at 25° C. for 16 h. The mixture was concentrated under reduced pressure. The residue was purified by flash chromatography (hexane/acetone, 4/1) to give 14f (209 mg, 77% yield) as a white solid.

Step f:

A mixture of 14f (49.0 mg, 0.08 mmol) and aqueous 2.5 N NaOH solution (0.4 mL, 1.0 mmol) in THF (1 mL) and MeOH (1 mL) was heated to 60° C. for 16 h. The cooled reaction mixture was rendered acidic with aqueous 1 N HCl solution and was extracted with EtOAc (2×). The combined organic layers were dried (MgSO$_4$), filtered and concentrated under reduced pressure to give compound 7003 (46 mg, 99% yield) as a white solid.

Example 15

(Entry 6002)

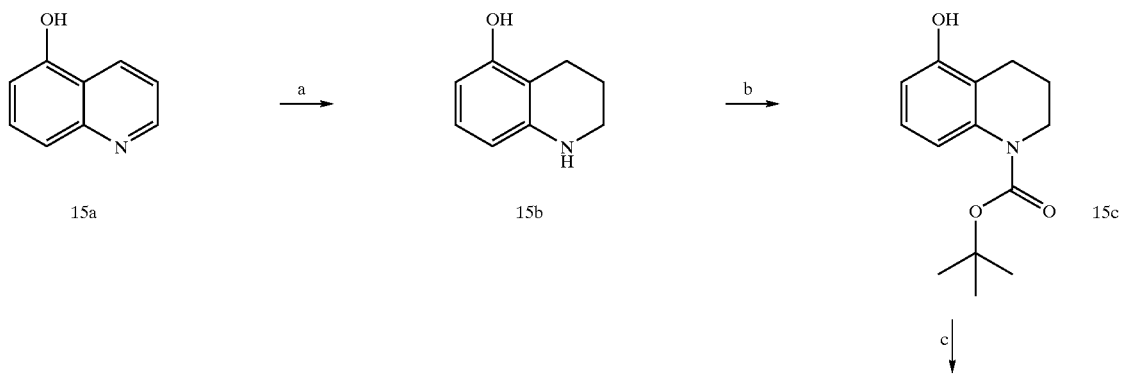

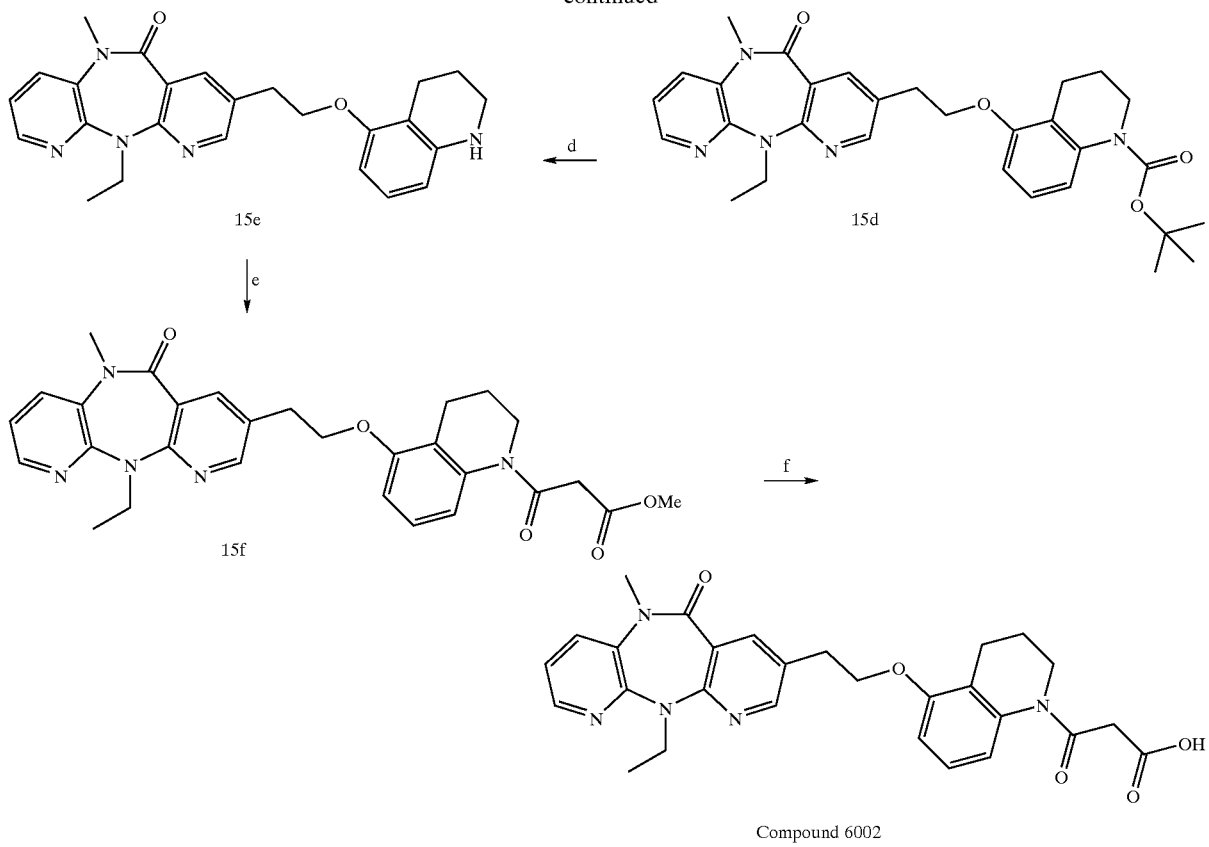

15e

15d

15f

Compound 6002

Step a:
Following the procedure described in Example 14 step a, 15a(435.5 mg, 3 mmol) gave compound 15b(425 mg, 95% yield) as a beige solid.

Step b:
Following the procedure described in Example 14 step c, 15b(415 mg, 2.8 mmol) gave compound 15c (460 mg, 66% yield) as a beige solid.

Step c:
A solution of DIAD (190 μL, 0.96 mmol) in THF (0.5 mL) was added dropwise to a solution of 5,11-dihydro-11-ethyl-8-(2-hydroxyethyl)-5-methyl-6H-dipyrido[3,2-b:2',3'-e][1,4]diazepin-6-one (228 mg, 0.76 mmol), 15c (150 mg, 0.47 mmol) and PPh$_3$ (254 mg, 0.97 mmol) in THF (10 mL) at 25° C. The reaction mixture was stirred at 25° C. for 16 h. The mixture was concentrated under reduced pressure. The residue was purified by flash chromatography (hexane/EtOAc, 6/4) to give 15d (212 mg, 40% yield) as a white solid.

Step d:
To a solution of 15d (201 mg, 0.4 mmol) in THF (2 mL) was added a 4 M solution of HCl in dioxane. The reaction mixture was stirred at 25° C. for 16 h. The mixture was concentrated under reduced pressure. The residue was diluted with CH$_2$Cl$_2$ and successively washed with saturated NaHCO$_3$ solution, water and brine, dried (MgSO$_4$), filtered and evaporated to dryness. The residue was purified by flash chromatography (hexane/EtOAc, 1/1) to give 15e (122 mg, 71% yield) as a white solid.

Step e:
To a solution of 15e (32 mg, 0.07 mmol) in CH$_2$Cl$_2$ (2 mL) was added methyl malonyl chloride (28.7 mg, 0.2 mmol) and Et$_3$N (50 μL, 0.35 mmol). After 16 h at room temperature the reaction was diluted in EtOAc and successively washed with water and brine, dried (MgSO$_4$), filtered and evaporated to dryness. The residue was purified by flash chromatography (hexane/EtOAc, 4/6) to give 15f (25.2 mg, 68% yield) as a white solid.

Step f:
Following the procedure described in Example 14 step f, 15f (23 mg, 0.04 mmol) gave compound 6002 (19.8 mg, 92% yield) as a white solid.

Employing the synthetic methods described in Examples 1–15, or analogous methods, the compounds defined, respectively, by each row of Tables 1 through 7, below, were made.

TABLE 1

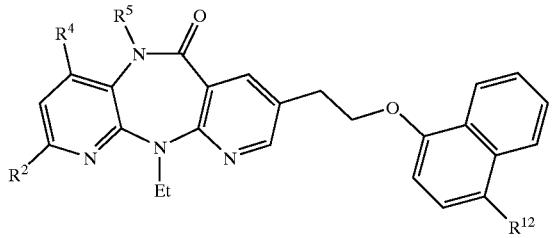

| Entry # | $R^2$ | $R^4$ | $R^5$ | $R^{12}$ | MS ES$^+$ (MH) |
|---|---|---|---|---|---|
| 1001 | H | H | Me | COOH | 469 |
| 1002 | Cl | H | Me | COOH | 503/505 |
| 1003 | Me | Me | Me | COOH | 483 |
| 1004 | F | Me | H | COOH | 487 |

TABLE 1-continued

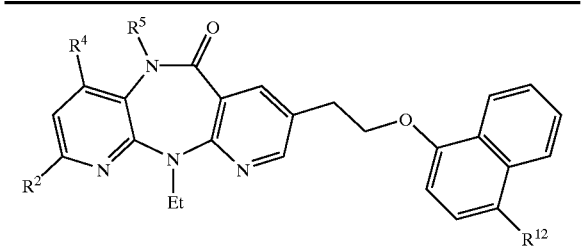

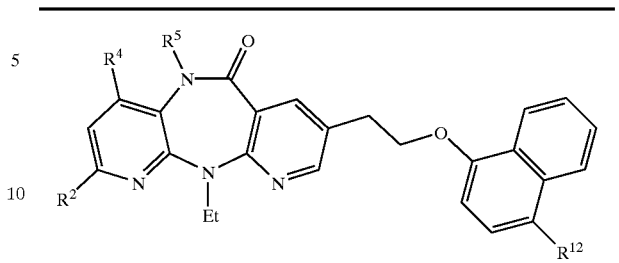

| Entry # | R² | R⁴ | R⁵ | R¹² | MS ES⁺ (MH) |
|---|---|---|---|---|---|
| 1005 | H | Me | H | COOH | 469 |
| 1006 | F | H | Me | COOH | 487 |
| 1007 | Cl | Me | H | COOH | 501/503(M−H) |
| 1008 | H | H | Me | CH₂COOH | 483 |
| 1009 | F | H | Me | CH₂COOH | 501 |
| 1010 | Cl | H | Me | CH₂COOH | 517/519 |
| 1011 | Me | H | Me | CH₂COOH | 497 |
| 1012 | Cl | Me | H | CH₂COOH | 517/517(M−H) |
| 1013 | H | Me | H | CH₂COOH | 483 |
| 1014 | F | Me | H | CH₂COOH | 501 |
| 1015 | H | H | Me | CH₂CONHNH₂ | 497 |
| 1016 | Cl | H | Me | CH₂CONHNH₂ | 531/533 |
| 1017 | NHNH₂ | H | Me | CH₂CONHNH₂ | 527 |
| 1018 | H | H | Me | CH₂CONH₂ | 482 |
| 1019 | H | H | Me | CH₂CONHSO₂Me | 560 |
| 1020 | H | H | Me | CH(Me)COOH | 497 |
| 1021 | H | H | Me | (CH₂)₂COOH | 497 |
| 1022 | Cl | H | Me | (CH₂)₂COOH | 531/533 |
| 1023 | F | H | Me | (CH₂)₂COOH | 515 |
| 1024 | H | Me | H | (CH₂)₂COOH | 497 |
| 1025 | Cl | Me | H | (CH₂)₂COOH | 527/531(M−H) |
| 1026 | Me | H | Me | (CH₂)₂COOH | 511 |
| 1027 | F | Me | H | (CH₂)₂COOH | 515 |
| 1028 | H | H | Me | *(see structure)* | 495 |
| 1029 | Cl | H | Me | *(see structure)* | 527/529(M−H) |
| 1030 | Cl | Me | H | *(see structure)* | 527/529(M−H) |
| 1031 | H | Me | H | *(see structure)* | 495 |
| 1032 | F | H | Me | *(see structure)* | 513 |
| 1033 | Me | H | Me | *(see structure)* | 509 |
| 1034 | F | Me | H | *(see structure)* | 513 |
| 1035 | H | H | Me | *(see structure)* | 509 |
| 1036 | Cl | H | Me | *(see structure)* | 543/545 |
| 1037 | F | H | Me | *(see structure)* | 527 |

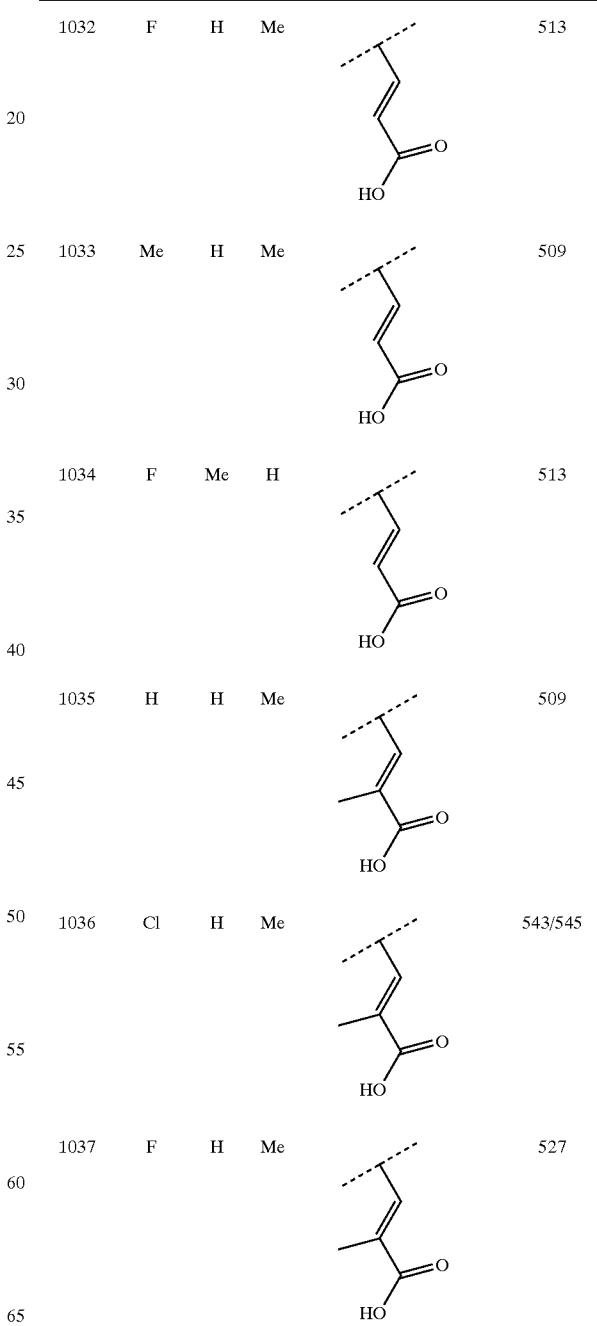

TABLE 1-continued

Structure: Tricyclic diazepinone core with R⁴, R⁵ on one side (R⁵ on N), R² on pyridine, N-Et, and ethyl-O-naphthyl with R¹² substituent.

| Entry # | R² | R⁴ | R⁵ | R¹² | MS ES⁺ (MH) |
|---|---|---|---|---|---|
| 1038 | Me | H | Me | (E)-2-methyl-but-2-enoic acid | 523 |
| 1039 | H | Me | H | (E)-2-methyl-but-2-enoic acid | 509 |
| 1040 | Cl | Me | H | (E)-2-methyl-but-2-enoic acid | 543/545 |
| 1041 | F | Me | H | (E)-2-methyl-but-2-enoic acid | 527 |
| 1042 | H | H | Me | CH₂CH(Me)—COOH | 511 |
| 1043 | F | H | Me | CH₂CH(Me)—COOH | 529 |
| 1044 | Cl | H | Me | CH₂CH(Me)—COOH | 545/547 |
| 1045 | Me | H | Me | CH₂CH(Me)—COOH | 525 |
| 1046 | H | Me | H | CH₂CH(Me)—COOH | 511 |
| 1047 | Cl | Me | H | CH₂CH(Me)—COOH | 543/545(M−H) |
| 1048 | H | H | Me | 3-methyl-but-2-enoic acid | 509 |
| 1049 | H | H | Me | 3-methylene-butanoic acid | 509 |
| 1050 | F | H | Me | cyclopropane carboxylic acid | 527 |
| 1051 | H | H | Me | CH(Me)CH₂COOH | 511 |

TABLE 2

Structure: Same tricyclic diazepinone core with R², R⁴, R⁵, N-Et, and ethyl-O-naphthyl-R¹².

| Entry # | R² | R⁴ | R⁵ | R¹² | MS ES⁺(MH) |
|---|---|---|---|---|---|
| 2001 | F | H | Me | NHSO₂Me | 536 |
| 2002 | F | H | Me | NHSO₂CF₃ | 590 |
| 2003 | H | H | Me | NHSO₂Me | 517 |
| 2004 | H | H | Me | SO₂NH₂ | 504 |
| 2005 | H | H | Me | SO₂NHAc | 546 |
| 2006 | H | H | Me | NHCO(CH₂)₂COOH | 540 |
| 2007 | H | H | Me | NHCOCH₂C(Me)₂COOH | 568 |
| 2008 | H | H | Me | SO₂NHCH₂COOH | 562 |
| 2009 | H | H | Me | CH₂COOH | 483 |
| 2010 | H | H | Me | COOH | 469 |
| 2011 | H | H | Me | CH₂CH₂COOH | 497 |
| 2012 | H | H | Me | CH₂CONHSO₂Me | 560 |
| 2013 | H | H | Me | (E,E)-penta-2,4-dienoic acid | 495 |
| 2014 | F | H | Me | (E)-pent-2-enoic acid | 513 |

TABLE 2-continued

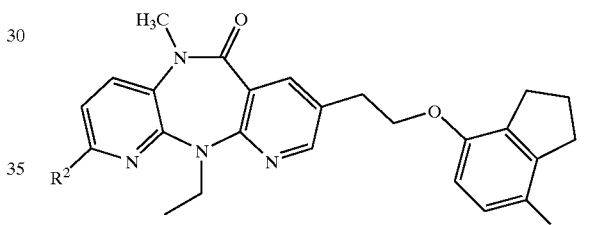

| Entry # | R² | R⁴ | R⁵ | R¹² | MS ES⁺(MH) |
|---|---|---|---|---|---|
| 2015 | F | Me | H | (CH=CH-C(=O)OH chain) | 513 |
| 2016 | Cl | H | Me | (CH=CH-C(=O)OH chain) | 529/531 |
| 2017 | Me | H | Me | (CH=CH-C(=O)OH chain) | 509 |
| 2018 | Cl | Me | H | (CH=CH-C(=O)OH chain) | 529/531 |
| 2019 | H | Me | H | (CH=CH-C(=O)OH chain) | 495 |
| 2020 | H | H | Me | CH₂CH₂CONHNH₂ | 511 |
| 2021 | H | H | Me | CH₂CH(Me)COOH | 511 |
| 2022 | H | H | Me | (CH=C(Me)-C(=O)OH chain) | 509 |

TABLE 3

| Entry # | R¹²ᵃ | R¹²ᵇ | MS ES⁺ (MH) |
|---|---|---|---|
| 3001 | H | COOH | 469 |
| 3002 | H | CONHNH₂ | 483 |
| 3003 | H | CONHC(Me)₂COOH | 554 |
| 3004 | H | CH₂COOH | 483 |
| 3005 | H | CH₂CONHNH₂ | 497 |
| 3006 | CH₃ | CH₂COOH | 483 |

TABLE 4

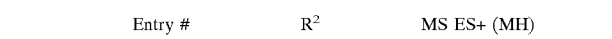

| Entry # | R² | MS ES+ (MH) |
|---|---|---|
| 4001 | H | 459 |
| 4002 | Cl | 493/495 |

TABLE 5

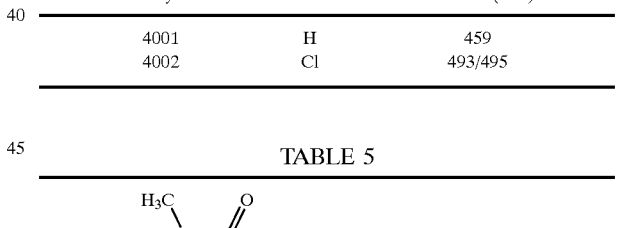

| Entry # | R² | R¹² | MS ES+ (MH) |
|---|---|---|---|
| 5001 | H | COOH | 473 |
| 5002 | Cl | COOH | 505/507(M−H) |
| 5003 | F | COOH | 491 |
| 5004 | Me | COOH | 487 |
| 5005 | OMe | COOH | 503 |
| 5006 | H | CH₂COOH | 487 |
| 5007 | Cl | CH₂COOH | 519/521(M−H) |
| 5008 | F | CH₂COOH | 505 |
| 5009 | H | CH₂CH₂COOH | 501 |
| 5010 | Cl | CH₂CH₂COOH | 535/537(M−H) |

TABLE 6

[Structure: 6-methyl-11-ethyl-dipyrido-diazepinone with ethyleneoxy-tetrahydroquinoline-N-R¹² substituent]

| Entry # | R¹² | MS ES+ (MH) |
|---|---|---|
| 6001 | CH$_2$COOH | 488 |
| 6002 | COCH$_2$COOH | 516 |

TABLE 7

[Structure: 6-methyl-11-ethyl-dipyrido-diazepinone with ethyleneoxy-tetrahydroisoquinoline-N-R¹² with COOH substituent]

| Entry # | R¹² | MS ES+ (MH) |
|---|---|---|
| 7002 | COOMe | 532 |
| 7003 | COO-t-Bu | 574 |
| 7004 | COMe | 516 |
| 7005 | SO$_2$Me | 552 |
| 7006 | CONHEt | 545 |
| 7007 | CONMe$_2$ | 545 |
| 7008 | SO$_2$NMe$_2$ | 581 |

Reverse TranscriptASE (RT) Assays

The assays are as described in WO 01/96338A1, the contents of which are hereby incorporated herein. The results are listed in Tables 8 as IC$_{50}$(nM) and EC$_{50}$(nM).

Table Legend:

A=>1000 nM; B=1000–100 nM; C=<100 nM; and NT=not tested.

TABLE 8

Inhibition of Wild type and mutant strains of RT for compounds of formula I

| Entry # | IC$_{50}$ WT RT (nM) | IC$_{50}$ V106A (nM) | IC$_{50}$ Y188L (nM) | IC$_{50}$ K103N/ Y181C (nM) | EC$_{50}$ WT RT (nM) | EC$_{50}$ V106A (nM) | EC$_{50}$ K103N/ Y181C (nM) |
|---|---|---|---|---|---|---|---|
| 1001 | C | A | A | B | C | NT | C |
| 1002 | C | B | B | C | C | NT | C |
| 1003 | C | A | A | B | NT | NT | NT |
| 1004 | C | B | A | B | NT | NT | NT |
| 1005 | C | B | A | B | NT | NT | NT |
| 1006 | C | A | A | B | C | NT | C |
| 1007 | C | B | A | B | C | NT | C |
| 1008 | C | A | A | B | C | NT | C |
| 1009 | C | A | A | B | C | NT | C |
| 1010 | C | A | A | B | C | NT | C |
| 1011 | C | A | A | B | NT | NT | NT |
| 1012 | C | B | A | B | C | NT | B |
| 1013 | C | A | A | A | NT | NT | NT |
| 1014 | C | B | A | B | NT | NT | NT |
| 1015 | C | B | B | C | NT | NT | C |
| 1016 | C | B | B | C | C | NT | C |
| 1017 | C | NT | NT | NT | NT | NT | NT |
| 1018 | C | B | A | C | NT | NT | NT |
| 1019 | C | A | A | B | C | NT | B |
| 1020 | C | A | A | B | C | NT | C |
| 1021 | C | A | A | B | C | NT | C |
| 1022 | C | B | A | B | C | NT | C |
| 1023 | C | A | A | B | C | NT | C |
| 1024 | C | B | A | A | NT | NT | NT |
| 1025 | C | B | A | B | C | NT | B |
| 1026 | C | A | A | B | NT | NT | NT |
| 1027 | C | B | A | B | NT | NT | NT |
| 1028 | C | A | B | B | C | NT | C |
| 1029 | C | B | B | B | C | NT | C |
| 1030 | C | C | A | B | C | NT | C |
| 1031 | C | B | A | B | C | NT | C |
| 1032 | C | B | B | B | C | NT | C |
| 1033 | C | B | B | B | C | NT | C |
| 1034 | C | C | A | B | C | NT | C |
| 1035 | C | A | A | B | C | NT | C |
| 1036 | C | B | A | B | C | NT | C |
| 1037 | C | A | A | B | C | NT | C |
| 1038 | C | A | A | B | C | NT | C |
| 1039 | C | B | A | B | NT | NT | NT |
| 1040 | C | B | A | B | C | NT | B |
| 1041 | C | B | A | B | NT | NT | NT |
| 1042 | C | A | A | B | C | NT | C |
| 1043 | C | A | A | B | NT | NT | NT |
| 1044 | C | A | A | B | C | NT | C |
| 1045 | C | A | A | B | NT | NT | NT |
| 1046 | C | A | A | A | NT | NT | NT |
| 1047 | C | B | A | B | NT | NT | NT |
| 1048 | C | A | A | B | C | NT | C |
| 1049 | C | A | A | B | C | NT | B |
| 1050 | C | B | B | B | C | NT | B |
| 1051 | C | A | A | B | C | NT | C |
| 2001 | C | B | B | C | C | NT | NT |
| 2002 | C | A | A | B | C | B | C |
| 2003 | C | A | A | B | NT | NT | C |
| 2004 | C | B | B | C | NT | NT | NT |
| 2005 | C | A | A | B | NT | NT | NT |
| 2006 | C | A | A | B | C | NT | B |
| 2007 | C | A | A | B | NT | NT | NT |
| 2008 | C | B | B | C | B | NT | B |
| 2009 | C | NT | NT | B | NT | NT | NT |
| 2010 | C | A | A | B | NT | NT | NT |
| 2011 | C | A | A | B | C | NT | B |
| 2012 | C | A | A | A | NT | NT | NT |
| 2013 | C | A | A | B | C | NT | C |
| 2014 | C | B | A | B | C | NT | B |
| 2015 | C | B | A | B | NT | NT | NT |
| 2016 | C | B | B | B | C | NT | B |
| 2017 | C | A | A | B | NT | NT | NT |
| 2018 | C | B | A | B | C | NT | B |
| 2019 | C | B | A | B | NT | NT | NT |
| 2020 | C | A | A | B | C | NT | B |
| 2021 | B | NT | NT | NT | NT | NT | NT |
| 2022 | C | A | A | B | NT | NT | NT |
| 3001 | C | B | A | B | NT | NT | NT |
| 3002 | C | C | A | B | C | NT | B |
| 3003 | C | B | A | B | C | NT | B |
| 3004 | C | B | A | A | NT | NT | NT |
| 3005 | C | C | B | B | C | NT | C |
| 3006 | C | B | B | B | C | B | C |
| 4001 | C | B | A | B | C | NT | C |
| 4002 | C | B | B | C | C | NT | C |
| 5001 | C | A | A | B | C | B | C |
| 5002 | C | A | B | B | C | NT | C |
| 5003 | C | A | B | B | C | NT | C |
| 5004 | C | A | B | B | C | NT | C |
| 5005 | C | A | B | B | C | NT | C |

TABLE 8-continued

Inhibition of Wild type and mutant strains of RT for compounds of formula I

| Entry # | $IC_{50}$ WT RT (nM) | $IC_{50}$ V106A (nM) | $IC_{50}$ Y188L (nM) | $IC_{50}$ K103N/ Y181C (nM) | $EC_{50}$ WT RT (nM) | $EC_{50}$ V106A (nM) | $EC_{50}$ K103N/ Y181C (nM) |
|---|---|---|---|---|---|---|---|
| 5006 | C | A | A | B | NT | NT | NT |
| 5007 | C | B | B | B | C | NT | C |
| 5008 | C | A | A | B | C | NT | C |
| 5009 | C | A | A | B | C | NT | C |
| 5010 | C | A | B | B | C | NT | C |
| 6001 | C | A | A | A | B | NT | NT |
| 6002 | C | NT | NT | NT | NT | NT | NT |
| 7002 | C | A | B | B | C | B | C |
| 7003 | C | A | B | B | C | NT | C |
| 7004 | C | A | A | B | B | NT | NT |
| 7005 | C | A | B | C | C | NT | NT |
| 7006 | C | B | A | B | B | NT | A |
| 7007 | C | B | B | C | C | NT | C |
| 7008 | C | B | B | C | C | NT | C |

What is claimed is:
1. A compound represented by formula I:

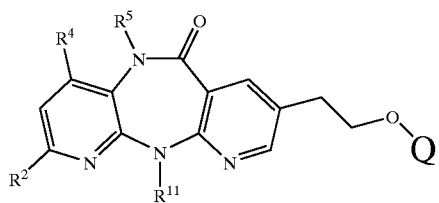

I wherein
$R^2$ is selected from the group consisting of H, halogen, $NHNH_2$, $(C_{1-4}alkyl)$, $O(C_{1-6})alkyl$, and haloalkyl;
$R^4$ is H or Me;
$R^5$ is H or $(C_{1-4}alkyl)$;
$R^{11}$ is $(C_{1-4}alkyl)$, $(C_{1-4}alkyl(C_{3-7})cycloalkyl)$, or $(C_{3-7})$ cycloalkyl; and
Q is naphthyl, fused phenyl($C_{4-7}$)cycloalkyl and fused phenyl-5, 6, or 7-membered saturated heterocycle having one N atom said Q being substituted with from 1 to 4-substituents each designated $R^{12}$ wherein each substituent designated $R^{12}$ has either the same definition as the group $R^{13}$ or is selected from the group consisting of $(C_{1-6})alkyl$, $(C_{3-7})cycloalkyl$, or $(C_{2-6})alkenyl$, said alkyl, cycloalkyl, or alkenyl being optionally substituted with $R^{13}$,
wherein $R^{13}$ defined as:
a) $NR^{13a}COR^{13}b$ wherein $R^{13}a$ and $R^{13}b$ are each independently H, $(C_{1-6})alkyl$, $(C_{3-7})cycloalkyl$ or $(C_{1-6})alkyl-(C_{3-7})cycloalkyl$, said alkyl, cycloalkyl or alkyl-cycloalkyl being optionally substituted with $R^{14}$;
b) $NR^{13c}SO_2R^{13d}$ wherein $R^{13c}$ is H, $(C_{1-6})alkyl$, $(C_{3-7})$ cycloalkyl or $(C_{1-6})alkyl-(C_{3-7})cycloalkyl$ and $R^{13d}$ is $(C_{1-6})alkyl$, haloalkyl, $(C_{3-7})cycloalkyl$ or $(C_{1-6})$ alkyl-$(C_{3-7})cycloalkyl$, said alkyl, cycloalkyl or alkyl-cycloalkyl being optionally substituted with $R^{14}$;
c) $COR^{13e}$ wherein $R^{13e}$ has the same definition as $R^{13d}$;
d) COOR wherein $R^{13f}$ has the same definition as $R^{13c}$;
e) $CONR^{13g}R^{13h}$ wherein $R^{13g}$ and $R^{13h}$ are both independently H, $(C_{1-6})alkyl$, $(C_{3-7})cycloalkyl$, or $(C_{1-6})alkyl-(C_{3-7})cycloalkyl$; or both $R^{13g}$ and $R^{13h}$ are covalently bonded together and to the nitrogen to which they are both bonded to form a 5, 6, or 7-membered saturated heterocycle; or $R^{13h}$ is $N(R^{13i})_2$ wherein each $R^{13i}$ is independently H, $(C_{1-6})alkyl$, $(C_{3-7})cycloalkyl$, or $(C_{1-6})alkyl-(C_{3-7})$ cycloalkyl or both $R^{13i}$ are covalently bonded together and to the nitrogen to which they are both bonded to form a 5, 6, or 7-membered saturated heterocycle, said alkyl, cycloalkyl, alkyl-cycloalkyl or heterocycle being optionally substituted with $R^{14}$;
f) $CONR^{13j}SO_2R^{13k}$ wherein $R^{13j}$ has the same definition as $R^{13c}$ and $R^{13k}$ has the same definition as $R^{13d}$; or
g) $SO_2R^{13l}$ wherein $R^{13l}$ is $(C_{1-6})alkyl$, $(C_{3-7})cycloalkyl$, or $(C_{1-6})alkyl-(C_{3-7})cycloalkyl$; or $R^{13l}$ is $NR^{13m}R^{13n}$ wherein $R^{13m}$ and $R^{13n}$ are both independently H, $(C_{1-6})alkyl$, $(C_{3-7})cycloalkyl$, or $(C_{1-6})alkyl-(C_{3-7})$ cycloalkyl; or both $R^{13m}$ and $R^{13n}$ are covalently bonded together and to the nitrogen to which they are both bonded to form a 5, 6, or 7-membered saturated heterocycle, said alkyl, cycloalkyl, alkyl-cycloalkyl or heterocycle being optionally substituted with $R^{14}$;
wherein $R^{14}$ is defined as:
$COOR^{14a}$, or $CON(R^{14b})_2$ wherein $R^{14a}$ and $R^{14b}$ are both independently H, $(C_{1-6})alkyl$, $(C_{3-7})cycloalkyl$, or $(C_{1-6})alkyl-(C_{3-7})cycloalkyl$; or both $R^{14b}$ are covalently bonded together and to the nitrogen to which they are both bonded to form a 5, 6, or 7-membered saturated heterocycle;
or a salt thereof.

2. A compound, according to claim 1, wherein
$R^2$ is selected from the group consisting of H, F, Cl, $NHNH_2$, $(C_{1-4}$ alkyl), and $CF_3$;
$R^4$ is H or Me;
$R^5$ is H or Me;
$R^{11}$ is $(C_{1-4}$ alkyl), or $(C_{3-7}$ cycloalkyl); and
Q is selected from the group consisting of:

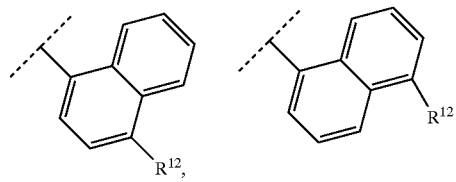

and

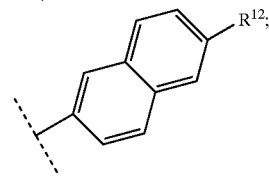

wherein
$R^{12}$ is selected from the group of: COOH, $(C_{1-6}$ alkyl)COOH, $(C_{2-6}alkenyl)COOH$, $(C_{1-6}$ alkyl)COO $(C_{1-6}$ alkyl), $(C_{1-6}$ alkyl)$CONH_2$, $(C_{3-7}cycloalkyl)$ COOH, 1–6 alkyl)$CONHNH_2$, $CH_2CONHSO_2CH_3$, $NHSO_2CH_3$, $NHSO_2CF_3$, $SO_2NHCOOH_3$, $SO_2NH_2$, $NHCO(C_{1-4}alkyl)COOH$, $NHCOOH_2C(CH_3)2COOH$, and $SO_2NHCH_2COOH$;
or a salt thereof.

3. A compound according to claim 1 wherein $R^2$ is selected from the group consisting of H, Cl, F, $NHNH_2$, $CH_3$, and OMe.

4. A compound according to claim 3, wherein $R^2$ is H, Cl, F, or $CH_3$.

5. A compound according to claim 4, wherein $R^2$ is H, Cl, or F.

6. A compound according to claim 1 wherein $R^4$ is H.

7. A compound according to claim 1 wherein $R^5$ is Me.

8. A compound according to claim 1 wherein $R^{11}$ is Et.

9. A compound according to claim 1 wherein Q is selected from the group consisting of: naphthyl, tetrahydronaphthyl, indanyl, tetrahydroquinolinyl, and tetrahydroisoquinolinyl, said Q being mono- or disubstituted with $R^{12}$.

10. A compound according to claim 1, wherein $R^{12}$ is $(C_{1-6})$alkyl, $(C_{24}$alkenyl or $(C_{3-7})$cycloalkyl, said alkyl, cycloalkyl or alkenyl being optionally substituted with $R^{13}$ wherein $R^{13}$ is selected from the group consisting of:
   a) COOH;
   b) $CONR^{13g}R^{13h}$ wherein $R^{3g}$ and $R^{13h}$ are both independently H, or $(C_{1-6})$alkyl optionally substituted with COOH; or $R^{13h}$ is $NH_2$; and
   c) $CONHSO_2CH_3$;

or $R^{12}$ is,
   a) $NHCO(C_{1-6})$alkyl-COOH;
   b) $NHSO_2CH_3$ or $NHSO_2CF_3$;
   c) $COOH_3$ or $COOH_2COOH$;
   d) $COOR^{13f}$ wherein $R^{13f}$ is H or $(C_{1-6})$alkyl;
   e) $CONR^{13g}R^{13h}$ wherein $R^{13g}$ and $R^{13h}$ are both independently H, or $(C_{1-6})$alkyl optionally substituted with COOH; or $R^{13h}$ is $NH_2$;
   f) $CONHSO_2CH_3$; or
   g) $SO_2Me$, $SO_2NH_2$, $SO_2NHCOOH_3$, $SO_2NHCH_2COOH$, or $SO_2N(CH_3)_2$.

11. A compound according to claim 10, wherein $R^{12}$ is $CH_3$, $CH_2COOH$, $(CH_2)_2COOH$, $CH(Me)COOH$, $CH(Me)CH_2COOH$, $CH_2CH(Me)COOH$, $CH_2CONH_2$, $CH_2CONHNH_2$, $CH_2CH_2CONHNH_2$, $CH_2CONHSO_2Me$,

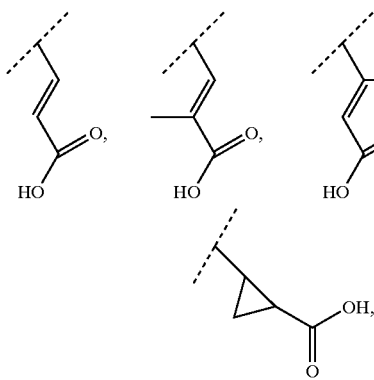

COOH, COOMe, COO-t-Bu, COMe, $COOH_2COOH$, $CONHC(Me)_2COOH$, $CONHNH_2$, CONHEt, $CONMe_2$, $NHCO(CH_2)2COOH$, $NHCOOH_2C(Me)_2COOH$, $NHSO_2CF_3$, $NHSO_2Me$, $SO_2Me$, $SO_2NMe_2$, $SO_2NH_2$, $SO_2NHAc$, or $SO_2NHCH_2COOH$.

12. A compound according to claim 11 wherein $R^{12}$ is $CH_3$, $CH_2COOH$, $(CH_2)_2COOH$, $CH_2CONH_2$, $CH_2CONHNH_2$,

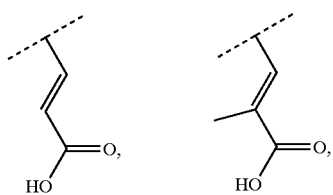

COOH, COOMe, COO-t-Bu, COMe, $CONMe_2$, $NHSO_2Me$, $SO_2Me$, $SO_2NMe_2$, $SO_2NH_2$, or $SO_2NHCH_2COOH$.

13. A compound according to claim 12 wherein $R^{12}$ is $CH_2CONH_2$, $CH_2CONHNH_2$, COOH, $CONMe_2$, $NHSO_2Me$, $SO_2Me$, $SO_2NMe_2$, $SO_2NH_2$, or $SO_2NHCH_2COOH$.

14. A compound according to claim 9 wherein Q is

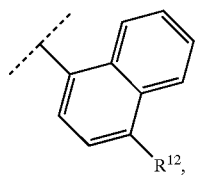

wherein $R^{12}$ is $(C_{1-6})$alkyl, $(C_{2-4}$alkenyl or $(C_{3-7})$cycloalkyl, said alkyl, cycloalkyl or alkenyl being optionally substituted with $R^{13}$ wherein $R^{13}$ is selected from the group consisting of:
   a) COOH;
   b) $CONH_2$, c) $CONHNH_2$; and
   d) $CONHSO_2CH_3$;

or $R^{12}$ is COOH.

15. A compound according to claim 14 wherein $R^{12}$ is $CH_2COOH$, $(CH_2)_2COOH$, $CH(Me)COOH$, $CH(Me)CH_2COOH$, $CH_2CH(Me)COOH$, $CH_2CONH_2$, $CH_2CONHNH_2$, $CH_2CONHSO_2Me$,

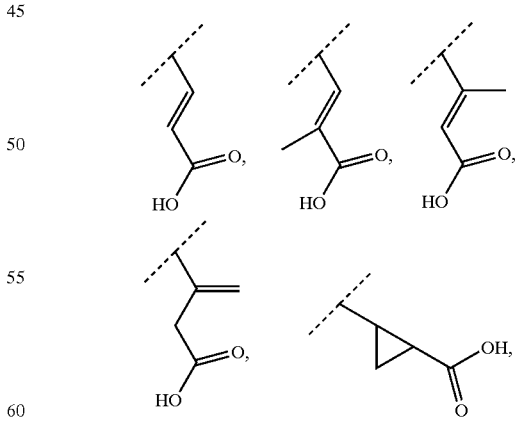

or COOH.

16. A compound according to claim 15 wherein $R^{12}$ is $CH_2COOH$, $(CH_2)_2COOH$, $CH_2CH(Me)COOH$, $CH_2CONH_2$, $CH_2CONHNH_2$,

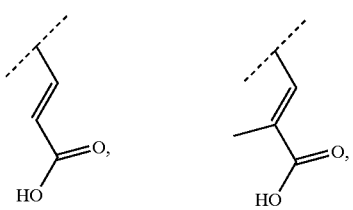

or COOH.

17. A compound according to claim 16 wherein $R^{12}$ is $CH_2COOH$, $(CH_2)_2COOH$, $CH_2CH(Me)COOH$, $CH_2CONH_2$, $CH_2CONHNH_2$, or COOH.

18. A compound according to claim 9 wherein Q is

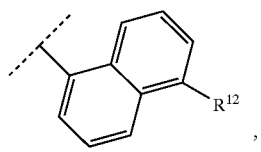

wherein $R^{12}$ is $(C_{1-6})$alkyl, or $(C_{2-4})$alkenyl, said alkyl or alkenyl being optionally substituted with $R^{13}$ wherein $R^{13}$ is selected from the group consisting of:

a) COOH;
b) $CONHNH_2$; and
c) $CONHSO_2CH_3$;

or $R^{12}$ is:

a) $NHCO(C_{1-6})$alkyl-COOH;
b) $NHSO_2CH_3$ or $NHSO_2CF_3$;
C) COOH; or
d) $SO_2NH_2$, $SO_2NHCOOH_3$, or $SO_2NHCH_2COOH$.

19. A compound according to claim 18 wherein $R^{12}$ is $CH_2COOH$, $(CH_2)_2COOH$, $CH_2CH(Me)COOH$, $CH_2CH_2CONHNH_2$, $CH_2CONHSO_2Me$,

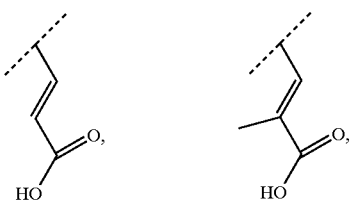

COOH, $NHCO(CH_2)_2COOH$, $NHCOOH_2C(Me)2COOH$, $NHSO_2CF_3$, $NHSO_2Me$, $SO_2NH_2$, $SO_2NHAc$, or $SO_2NHCH_2COOH$.

20. A compound according to claim 19 wherein $R^{12}$ is $(CH_2)_2COOH$,

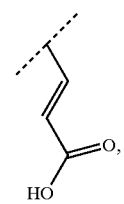

$NHSO_2Me$, $SO_2NH_2$, or $SO_2NHCH_2COOH$.

21. A compound according to claim 20 wherein $R^{12}$ is $(CH_2)_2COOH$, $NHSO_2Me$, $SO_2NH_2$, or $SO_2NHCH_2COOH$.

22. A compound according to claim 9 wherein Q is

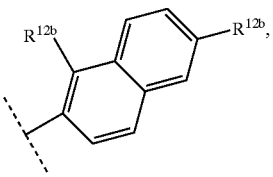

wherein $R^{12b}$ is $(C_{1-6})$alkyl substituted with wherein is selected from the group consisting of:

a) COOH; and
b) $CONHNH_2$;

or $R^{12b}$ is:

a) COOH;
b) $CONHNH_2$ or $CONHC(Me)_2COOH$;

and $R^{12a}$ is H or $CH_3$.

23. A compound according to claim 22 wherein R is $CH_2COOH$ and $R^{12a}$ is $CH_3$.

24. A compound according to claim 9 wherein Q is

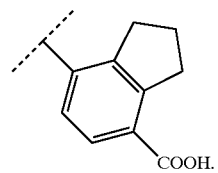

25. A compound according to claim 9 wherein Q is

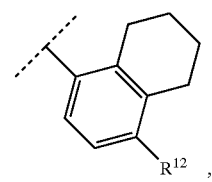

wherein $R^{12}$ $(C_{1-6})$alkyl substituted with COOH or $R^{12}$ is COOH.

26. A compound according to claim 25 wherein $R^{12}$ is $CH_2COOH$, $CH_2CH_2COOH$ or COOH.

27. A compound according to claim 9 wherein Q is

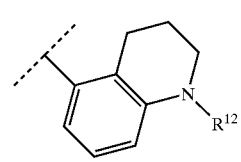

wherein $R^{12}$ is $CH_2COOH$ or $COOH_2COOH$.

28. A compound according to claim 9 wherein Q is

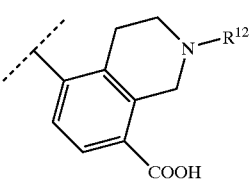

wherein $R^{12}$ is
a) $COOH_3$;
b) $COO(C_{1-6})$alkyl;

c) c) CONHEt, CONMe$_2$; or d) SO$_2$Me or SO$_2$N(CH$_3$)$_2$.

29. A compound according to claim 28 wherein R$^{12}$ is COMe, CONMe$_2$, COOMe, COO$^t$Bu, SO$_2$Me, or SO$_2$NMe$_2$.

30. A compound according to claim 29 wherein R$^{12}$ is CONMe$_2$, CO$_2$Me, COOTBU or SO$_2$NMe$_2$.

31. A compound selected from the group consisting of species 1001 through 1051, or a pharmaceutically acceptable salt thereof, wherein each of said species is a compound of the formula

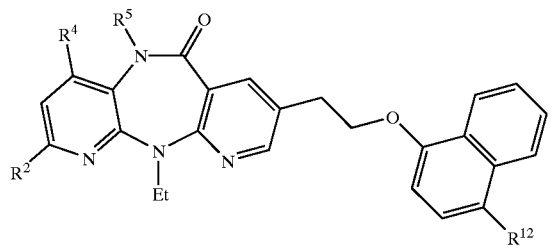

wherein R$^2$, R$^4$ R$^5$ and R$^{12}$ are as defined in the respective row of the following Table A

TABLE A

| Species # | R$^2$ | R$^4$ | R$^5$ | R$^{12}$ |
|---|---|---|---|---|
| 1001 | H | H | Me | COOH |
| 1002 | Cl | H | Me | COOH |
| 1003 | Me | H | Me | COOH |
| 1004 | F | Me | H | COOH |
| 1005 | H | Me | H | COOH |
| 1006 | F | H | Me | COOH |
| 1007 | Cl | Me | H | COOH |
| 1008 | H | H | Me | CH$_2$COOH |
| 1009 | F | H | Me | CH$_2$COOH |
| 1010 | Cl | H | Me | CH$_2$COOH |
| 1011 | Me | H | Me | CH$_2$COOH |
| 1012 | Cl | Me | H | CH$_2$COOH |
| 1013 | H | Me | H | CH$_2$COOH |
| 1014 | F | Me | H | CH$_2$COOH |
| 1015 | H | H | Me | CH$_2$CONHNH$_2$ |
| 1016 | Cl | H | Me | CH$_2$CONHNH$_2$ |
| 1017 | NHNH$_2$ | H | Me | CH$_2$CONHNH$_2$ |
| 1018 | H | H | Me | CH$_2$CONH$_2$ |
| 1019 | H | H | Me | CH$_2$CONHSO$_2$Me |
| 1020 | H | H | Me | CH(Me)COOH |
| 1021 | H | H | Me | (CH$_2$)$_2$COOH |
| 1022 | Cl | H | Me | (CH$_2$)$_2$COOH |
| 1023 | F | H | Me | (CH$_2$)$_2$COOH |
| 1024 | H | Me | H | (CH$_2$)$_2$COOH |
| 1025 | Cl | Me | H | (CH$_2$)$_2$COOH |
| 1026 | Me | H | Me | (CH$_2$)$_2$COOH |
| 1027 | F | Me | H | (CH$_2$)$_2$COOH |
| 1028 | H | H | Me | *CH=CH-COOH* |
| 1029 | Cl | H | Me | *CH=CH-COOH* |
| 1030 | Cl | Me | H | *CH=CH-COOH* |
| 1031 | H | Me | H | *CH=CH-COOH* |
| 1032 | F | H | Me | *CH=CH-COOH* |
| 1033 | Me | H | Me | *CH=CH-COOH* |
| 1034 | F | Me | H | *CH=CH-COOH* |
| 1035 | H | H | Me | *C(Me)=CH-COOH* |

TABLE A-continued

| Species # | R² | R⁴ | R⁵ | R¹² |
|---|---|---|---|---|
| 1036 | Cl | H | Me | (structure) |
| 1037 | F | H | Me | (structure) |
| 1038 | Me | H | Me | (structure) |
| 1039 | H | Me | H | (structure) |
| 1040 | Cl | Me | H | (structure) |
| 1041 | F | Me | H | (structure) |
| 1042 | H | H | Me | CH₂CH(Me)—COOH |
| 1043 | F | H | Me | CH₂CH(Me)—COOH |
| 1044 | Cl | H | Me | CH₂CH(Me)—COOH |
| 1045 | Me | H | Me | CH₂CH(Me)—COOH |
| 1046 | H | Me | H | CH₂CH(Me)—COOH |
| 1047 | Cl | Me | H | CH₂CH(Me)—COOH |
| 1048 | H | H | Me | (structure) |
| 1049 | H | H | Me | (structure) |
| 1050 | F | H | Me | (structure) |
| 1051 | H | H | Me | CH(Me)CH₂COOH |

32. A compound selected from the group consisting of species 2001 through 1022, or a pharmaceutically acceptable salt thereof, wherein each of said species is a compound of the formula

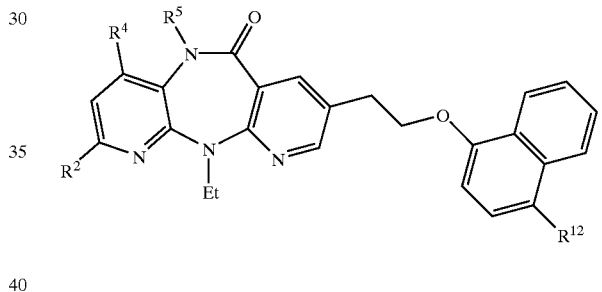

wherein wherein $R^2$, $R^4$, $R^5$ and $Q^{ii}$ are as defined in the respective row of the following Table B

TABLE B

| Species # | R² | R⁴ | R⁵ | R¹² |
|---|---|---|---|---|
| 2001 | F | H | Me | NHSO₂Me |
| 2002 | F | H | Me | NHSO₂CF₃ |
| 2003 | H | H | Me | NHSO₂Me |
| 2004 | H | H | Me | SO₂NH₂ |
| 2005 | H | H | Me | SO₂NHAc |
| 2006 | H | H | Me | NHCO(CH₂)₂COOH |
| 2007 | H | H | Me | NHCOCH₂C(Me)₂COOH |
| 2008 | H | H | Me | SO₂NHCH₂COOH |
| 2009 | H | H | Me | CH₂COOH |
| 2010 | H | H | Me | COOH |
| 2011 | H | H | Me | CH₂CH₂COOH |
| 2012 | H | H | Me | CH₂CONHSO₂Me |
| 2013 | H | H | Me | 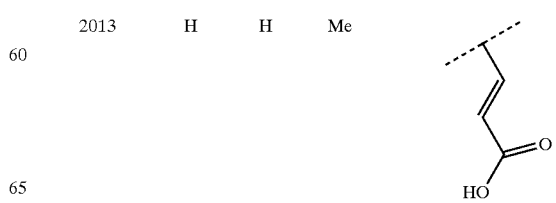 |

TABLE B-continued

| Species # | R² | R⁴ | R⁵ | R¹² |
|---|---|---|---|---|
| 2014 | F | H | Me | (CH=CH-CH=CH-COOH chain) |
| 2015 | F | Me | H | (CH=CH-CH=CH-COOH chain) |
| 2016 | Cl | H | Me | (CH=CH-CH=CH-COOH chain) |
| 2017 | Me | H | Me | (CH=CH-CH=CH-COOH chain) |
| 2018 | Cl | Me | H | (CH=CH-CH=CH-COOH chain) |
| 2019 | H | Me | H | (CH=CH-CH=CH-COOH chain) |
| 2020 | H | H | Me | CH₂CH₂CONHNH₂ |
| 2021 | H | H | Me | CH₂CH(Me)COOH |
| 2022 | H | H | Me | (CH=CH-C(Me)=CH-COOH chain) |

33. A compound selected from the group consisting of species 3001 through 3006, or a pharmaceutically acceptable salt thereof, wherein each of said species is a compound of the formula

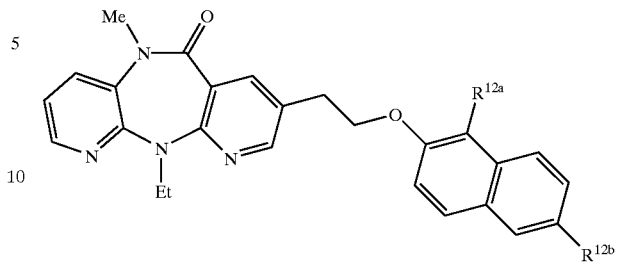

wherein $R^{12a}$ and $R^{12}$ are as defined in the respective row of the following Table C

TABLE C

| Species # | R¹²ᵃ | R¹²ᵇ |
|---|---|---|
| 3001 | H | COOH |
| 3002 | H | CONHNH₂ |
| 3003 | H | CONHC(Me)₂COOH |
| 3004 | H | CH₂COOH |
| 3005 | H | CH₂CONHNH₂ |
| 3006 | CH₃ | CH₂COOH |

34. A compound of the formula

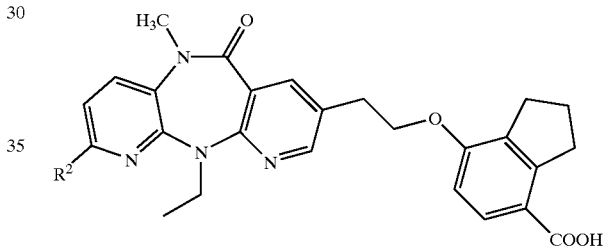

wherein $R^2$ is H or Cl, or a pharmaceutically acceptable salt thereof.

35. A compound selected from the group consisting of species 5001 through 5010, or a pharmaceutically acceptable salt thereof, wherein each of said species is a compound of the formula

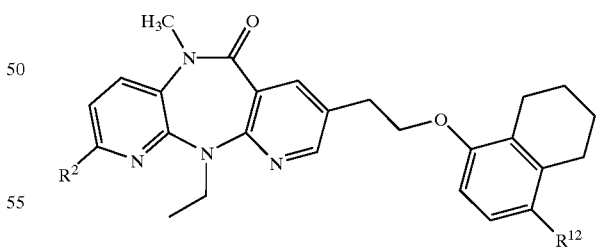

wherein $R^2$ and $R^{12}$ are as defined in the respective row of the following Table D

TABLE D

| Species # | R² | R¹² |
|---|---|---|
| 5001 | H | COOH |
| 5002 | Cl | COOH |

TABLE D-continued

| Species # | $R^2$ | $R^{12}$ |
| --- | --- | --- |
| 5003 | F | COOH |
| 5004 | Me | COOH |
| 5005 | OMe | COOH |
| 5006 | H | $CH_2COOH$ |
| 5007 | Cl | $CH_2COOH$ |
| 5008 | F | $CH_2COOH$ |
| 5009 | H | $CH_2CH_2COOH$ |
| 5010 | Cl | $CH_2CH_2COOH$ |

36. A compound of the formula:

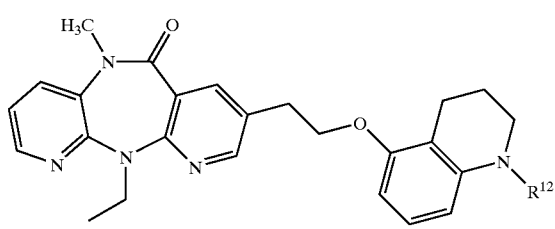

wherein $R^{12}$ is —$CH_2COOH$ or —$COOH_2COOH$, or a pharmaceutically acceptable salt thereof.

37. A compound selected from the group consisting of species 7001 through 7008, or a pharmaceutically acceptable salt thereof, wherein each of said species is a compound of the formula

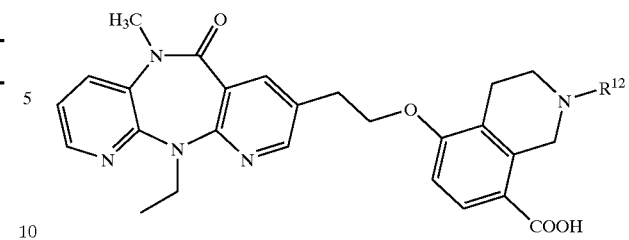

wherein $R^2$ as defined in the respective row of the following Table E

TABLE E

| Species # | $R^{12}$ |
| --- | --- |
| 7002 | COOMe |
| 7003 | COO-t-Bu |
| 7004 | COMe |
| 7005 | $SO_2Me$ |
| 7006 | CONHEt |
| 7007 | $CONMe_2$ |
| 7008 | $SO_2NMe_2$ |

38. A pharmaceutical composition comprising a compound according to claim 1 and a pharmaceutically acceptable carrier.

39. A method for the treatment of HIV-1 infection, which comprises administering to a patient atherapeutic amount of a compound according to claim 1.

40. A method for preventing perinatal transmission of HIV-1 from mother to baby, comprising administering a compound according to claim 1 to the mother before giving birth.

* * * * *